United States Patent
Hug et al.

(10) Patent No.: US 11,728,078 B2
(45) Date of Patent: Aug. 15, 2023

(54) MAGNETIC PARTICLES AND USES THEREOF

(71) Applicant: Roche Molecular Systems, Inc., Pleasanton, CA (US)

(72) Inventors: Stephan Hug, Penzberg (DE); Fangbing Liu, Marlborough, MA (US); Nancy Schoenbrunner, Marlborough, MA (US); Martin Eduardo Silvestre, Penzberg (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 540 days.

(21) Appl. No.: 16/860,968

(22) Filed: Apr. 28, 2020

(65) Prior Publication Data

US 2020/0265979 A1    Aug. 20, 2020

Related U.S. Application Data

(63) Continuation of application No. PCT/EP2018/079829, filed on Oct. 31, 2018.

(60) Provisional application No. 62/579,380, filed on Oct. 31, 2017.

(30) Foreign Application Priority Data

Oct. 31, 2017 (EP) .................................. 17199299

(51) Int. Cl.

| | |
|---|---|
| H01F 1/00 | (2006.01) |
| H01F 1/34 | (2006.01) |
| C01G 49/08 | (2006.01) |
| C12N 15/10 | (2006.01) |
| C12Q 1/686 | (2018.01) |
| H01F 41/02 | (2006.01) |

(52) U.S. Cl.
CPC ............. H01F 1/344 (2013.01); C01G 49/08 (2013.01); C12N 15/1013 (2013.01); C12Q 1/686 (2013.01); H01F 1/0018 (2013.01); H01F 41/0206 (2013.01); C01P 2004/03 (2013.01); C01P 2004/62 (2013.01); C01P 2004/86 (2013.01); C01P 2006/42 (2013.01)

(58) Field of Classification Search
CPC ...... H01F 1/0054; H01F 1/0018; H01F 1/344; H01F 41/0206; C01G 49/08; C01P 2004/62; C01P 2004/64; C01P 2004/86; C01P 2006/42
See application file for complete search history.

(56) References Cited

U.S. PATENT DOCUMENTS

| | | | | |
|---|---|---|---|---|
| 6,440,322 | B1 * | 8/2002 | Kim ................. | H01F 1/447 252/62.55 |
| 2004/0067503 | A1 * | 4/2004 | Tan .................. | B82Y 15/00 436/526 |
| 2006/0007526 | A1 * | 1/2006 | Cannas ............. | G09F 9/375 359/296 |
| 2008/0281087 | A1 * | 11/2008 | Markert-Hahn ..... | C12Q 1/6827 536/25.3 |
| 2012/0080878 | A1 * | 4/2012 | Kecht .............. | B42D 25/00 283/85 |
| 2017/0159043 | A1 | 6/2017 | Hennig et al. | |

FOREIGN PATENT DOCUMENTS

| | | |
|---|---|---|
| CN | 103714929 A | 4/2014 |
| EP | 2110175 A1 | 10/2009 |
| WO | 2001/088540 A1 | 11/2001 |
| WO | 2006/136314 A1 | 12/2006 |
| WO | 2008/081917 A1 | 7/2008 |
| WO | 2014090838 A1 | 6/2014 |

OTHER PUBLICATIONS

EP, Search Report, EESR, dated Jun. 7, 2018, Whole Document, N/A.
International Search Report dated Feb. 5, 2019 in Application No. PCT/EP2018/079829, 13 pages.
Liu, J., et al., "HighlyWater-Dispersible Biocompatible Magnetite Particles with Low Cytotoxicity Stabilized by Citrate Groups", Angewandte Chemie International Edition, Jul. 27, 2009, pp. 5875-5879, vol. 48, No. 32.

* cited by examiner

*Primary Examiner* — Matthew E. Hoban
*Assistant Examiner* — Lynne Edmondson
(74) *Attorney, Agent, or Firm* — FisherBroyles, LLP; Jason M. Pass

(57) ABSTRACT

The disclosure provides improved magnetic glass particles for use in nucleic acid capture, enrichment, analysis, and/or purification. Various modifications to the disclosed compositions and methods of using the same, as well as devices and kits are described.

19 Claims, 8 Drawing Sheets

Solvothermal Reaction:

$6 FeCl_3 + 2 C_2H_6O_2 + 6 H_2O \rightarrow 2 Fe_3O_4 + C_4H_6O_2 + 18 HCl$ $Si(OEt)_4 + 4 H_2O \rightarrow Si(OH)_4 + 4 EtOH \rightarrow (SiO_2)_x + 2x H_2O$ Fig. 3B
$$Na_2SiO_3 + 2\ HCl \rightarrow H_2SiO_3 + 2\ NaCl \rightarrow (SiO_2)_x + x\ H_2O$$
Fig. 4A
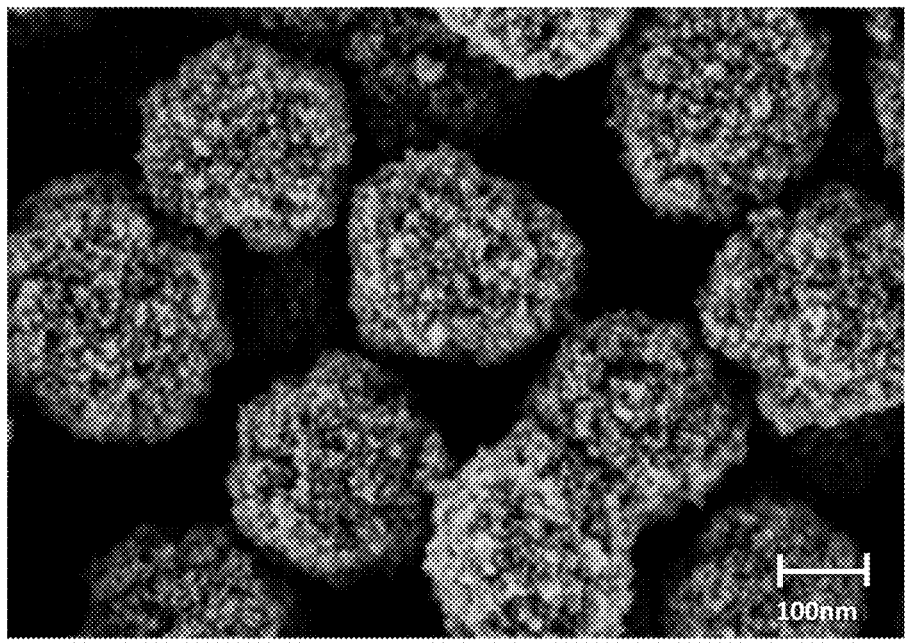
Fig. 4B
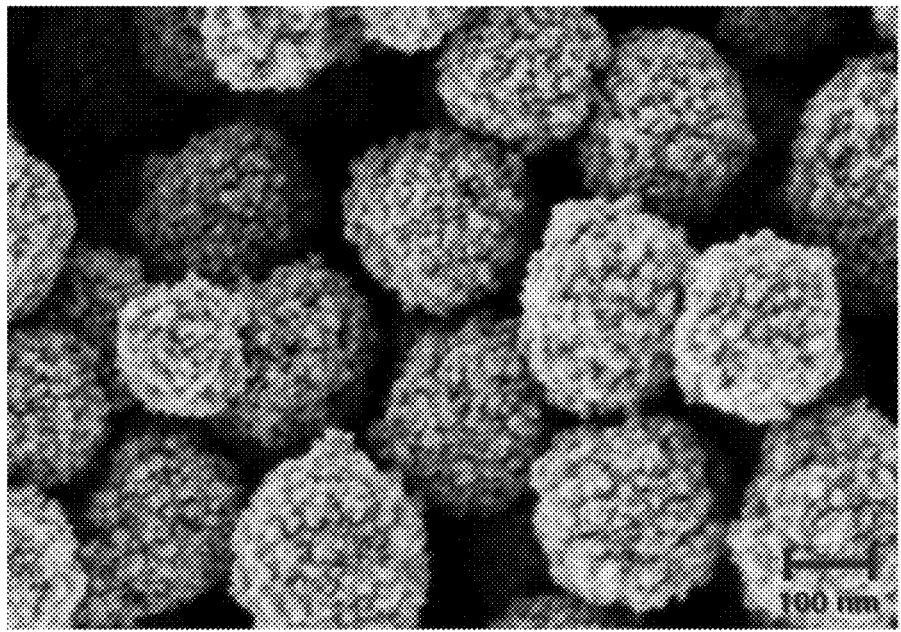

100nm

100nm under 35 U.S.C. § 111(a) of International Patent Application No. PCT/EP2018/079829, filed Oct. 31, 2018, which claims the benefit and priority of U.S. Provisional Patent Application No. 62/579,380, filed Oct. 31, 2017, and European Patent Application 17199299.3, filed Oct. 31, 2017, both of which applications are incorporated herein by reference.

MAGNETIC PARTICLES AND USES THEREOF

CROSS-REFERENCES TO RELATED APPLICATIONS

This application is a continuation application filed under 35 U.S.C. § 111(a) of International Patent Application No. PCT/EP2018/079829, filed Oct. 31, 2018, which claims the benefit and priority of U.S. Provisional Patent Application No. 62/579,380, filed Oct. 31, 2017, and European Patent Application 17199299.3, filed Oct. 31, 2017, both of which applications are incorporated herein by reference.

FIELD OF THE DISCLOSURE

Improved magnetic glass particles are disclosed for use in a sample processing tubule configured to perform nucleic acid analysis, capture, enrichment, and purification.

BACKGROUND OF THE DISCLOSURE

Many biological materials, especially nucleic acids, present special challenges in terms of isolating them from their natural environment. On the one hand, they are often present in very small concentrations and, on the other hand, they are often found in the presence of many other solid and dissolved substances that make them difficult to isolate or to measure, in particular in biospecific assays.

In the field of nucleic acid purification, magnetic silica particles are widely used. Ferrimagnetic nanoparticles commonly are not commercially available and only known from academic publications. Such publications include nanoparticles with silica coatings (Chen et al; J. of alloys and compounds 497 (2010) 221-227; Wang et al; Bioresource Technology 101 (2010) 8931-8935; Reza et al; Cent. Eu. J. Chem 5 (2010) 1041-1048). However, numerous magnetic silica particles are commercially available, most of which show superparamagnetic behavior. Commercially available particles are usually made of magnetic cores with a silane coating according to the Stober method (Stober et al., *J. Colloid Interface Sci.*, 1968, 26, 62). In the few known examples, the silica source is based on soluble silicates (liquid glass) (Philipse et al., Langmuir, 1994, 10, 92-99; Bolle et al., 2015, EP2916327B1). For the magnetic core, either nanoparticles ranging from 3-10 nm with superparamagnetic behavior or nanoparticles greater than 60 nm with ferromagnetic behavior are typically used. An example for nanoparticles of greater than 60 nm with superparamagnetic behavior was shown by Liu et al. (Angew. Chem. Int. Ed., 2009, 48, 5875-5879) but such particles have not been used for nucleic acid purification. EP2110175 discloses the use of coated magnetic beads in PCR applications, wherein the magnetic beads have a magnetic core made up from metals or alloys covered with a polymer or a silica coating. However, EP2110175 does not disclose any preferred properties of beads (e.g., superparamagnetic properties) nor solvothermal production of such beads. WO2014/090838 discloses magnetic particles having a $SiO_2$ containing surface that represents 25-85% (by weight) of the magnetic silica particles and having a particle size of 30 μm or less. Herein, the magnetic core particles are produced using a precipitation reaction. In a second step the particles are coated with silica, wherein several core particles or agglomerates thereof are coated to form magnetic silica particles. Hence, the magnetic silica particles exhibit a thick silica coating. Moreover, the production method disclosed in WO 2014/090838 does not enable the production of supraparticles (i.e., defined aggregates of magnetic nanoparticles), wherein only the supraparticles are covered with a thin silica coating. However, particles having a thick silica coating have been shown to not be suitable in systems with challenging and demanding reaction conditions.

The use of such particles in nucleic acid purification under certain conditions (as may be found in a sample processing tubule and/or as required to enable a short turnaround time) requires that particles show a strong magnetic response, low magnetic remanence and a high and quick binding capacity for nucleic acids in combination with fast elution properties of the nucleic acids, which is not the case for such commercially available particles. Hence, the object of the present description is the provision of particles that afford these properties.

SUMMARY OF THE DISCLOSURE

In one aspect, the present disclosure provides a composition of magnetic beads comprising (a) a stabilizer and a magnetic core produced under solvothermal conditions, (b) a liquid-glass coating, wherein the magnetic bead is superparamagnetic. In some embodiments, the magnetic bead has a particle size of great than 100 nm. In some embodiments, the diameter is between about 80-500 nm, more specifically between about 150-450 nm, more specifically between about 200-400 nm, and even more specifically between about 250-400 nm. In certain embodiments, the magnetic bead has a particle size of between 200-400 nm. In some embodiments, the diameter of the magnetic core is between about 50-450 nm, more specifically between about 100-400 nm, more specifically between about 150-350 nm, more specifically about 200-350 nm. In particular embodiments, the magnetic core is between about 250-320 nm, more specifically between about 260-300 nm, more specifically between about 270-290 nm. In some embodiments, the magnetic bead has a saturation magnetization of 30-80 $Am^2/kg$, more specifically 50-70 $Am^2/kg$. In some embodiments, the magnetic bead has a magnetic remanence below 5 $Am^2/kg$, more specifically below 3 $Am^2/kg$, even more specifically below 2 $Am^2/kg$. In some embodiments, the magnetic bead has a magnetic remanence below 3 $Am^2/kg$. In some embodiments, the liquid-glass coating comprises a silicate. In particular embodiments the silicate is selected from the group consisting of sodium silicate, potassium silicate, calcium silicate, lithium silicate, and magnesium silicate. In some embodiments, the silicate is sodium silicate. In some embodiments, the liquid-glass coating has a thickness of 20 nm or less. In certain embodiments, the liquid-glass coating has a thickness of 10 nm or less. In some embodiments, the magnetic core is a defined aggregate of magnetic nanoparticles with the stabilizer. In some embodiments, the stabilizer is selected from the group consisting of citrate, histidine, cetyltrimethylammonium bromide (CTAB), cetyltrimethylammonium chloride (CTAC), sodium oleate, and polyacrylic acid. In a particular embodiment, the stabilizer is sodium citrate. In some embodiments, the magnetic core is a defined aggregate of magnetic nanoparticles with at least one stabilizer. In some embodiments, the magnetic core is a defined aggregate of magnetic nanoparticles, wherein the magnetic nanoparticles have a size of <30 nm and wherein the diameter of the defined aggregate of magnetic nanoparticles is between 50-450 nm, more specifically between about 100-400 nm, more specifically between about 150-350 nm, more specifically about 200-350 nm. Herein, the magnetic core provides for superparamagnetic properties. In one embodiment the stabilizer is present or is added in situ during the formation of said defined aggregate of magnetic nanoparticles. In some embodiments, the at least one stabilizer is selected from the group consisting of citrate, histidine, cetyl trimethylammonium bromide (CTAB), cetyl trimethylammonium chloride (CTAC), sodium oleate, and polyacrylic acid, or mixtures of two or more thereof. In a particular embodiment, the mixture of stabilizers comprises sodium citrate. In some embodiments, the magnetic core is $Fe_3O_4$, $\alpha\text{-}Fe_2O_3$, $\gamma\text{-}Fe_2O_3$, $MnFe_xO_y$, $CoFe_xO_y$, $NiFe_xO_y$, $CuFe_xO_y$, $ZnFe_xO_y$, $CdFe_xO_y$, $BaFe_xO$ and $SrFe_xO$, wherein x and y vary depending on the method of synthesis, and wherein x is preferably an integer of from 1 to 3 inclusive, more preferably 2, and wherein y is preferably 3 or 4 most preferably, $Fe_3O_4$. In particular embodiments the magnetic core is a magnetite core. In some embodiments, solvothermal conditions are conditions including 190-250° C. and increased pressure of 1-20 bar. In some embodiments, the magnetic beads are substantially spherical.

In another aspect, the present disclosure provides a suspension of magnetic beads comprising a composition indicated above and a liquid, wherein the suspension is mixed to homogeneity. In some embodiments, the suspension comprises between 5 to 200 mg/mL magnetic beads. In other embodiments, the suspension comprises between 5 to 100 mg/mL magnetic beads. In other embodiments, the suspension comprises between 5 to 60 mg/mL magnetic beads. In certain embodiments, the suspension comprises between 25 to 50 mg/mL magnetic beads. In some embodiments, the liquid comprises an aqueous buffered solution. In some embodiments, the aqueous buffered solution comprises Tris-hydroxymethylamine (TRIS), phosphate, or N-(2-Hydroxyethyl)piperazine-N'-(2-ethanesulfonic acid) (HEPES), and mixtures thereof. In some embodiments, the aqueous buffered solution further comprises a chaotropic agent. In certain embodiments, the chaotropic agent is present in the suspension at a concentration of between 2-8 mol/L. In some embodiments, the chaotropic agent is selected from the group consisting of sodium iodide, sodium perchlorate, guanidinium thiocyanate, guanidinium isothiocyanate, and guanidinium hydrochlorite.

In another aspect, the present disclosure provides a device configured to perform a nucleic acid analysis of a sample, said device comprising
  a. a sample introduction port adapted to receive a sample aliquot;
  b. a compartment comprising a composition comprising magnetic beads, as described herein; and
  c. a PCR analysis region comprising one or more additional compartments each configured to conduct one or more steps of said PCR analysis comprising reagent preparation, target enrichment, inhibitor removal, nucleic acid extraction, amplification, and real-time detection.

In another aspect, the present disclosure provides a kit comprising a device as disclosed herein. In some embodiments, the kit includes any manufacture (e.g., a package or a container) including at least one device for specifically amplifying, capturing, tagging/converting or detecting a target nucleic acid sequence as described herein, wherein the compositions described herein are included in the device or provided as a separate kit component, vial or container. In some embodiments, the kit further includes any one of instructions for use, supplemental reagents, control materials, and/or components or modules used in the amplification methods described herein or a step thereof.

In another aspect, the present disclosure provides a kit comprising the composition of disclosed above. In some embodiments, the composition may be provided in a device described herein. In some embodiments, the composition is provided in a package or a container. In some embodiments, the kit further includes at least one of the following components: nucleoside triphosphates, nucleic acid polymerase, and buffers necessary for the function of the nucleic acid polymerase. In some embodiments, the kit components are included in the kit as separate components, in separate vials or containers. In some embodiments, one of more of the kit components is included in the kit in the same vial or container. In some embodiments, the kit further comprises an eluent or elution buffer. In some embodiments, the kit further contains a nucleic acid polymerase enzyme having 5' to 3' exonuclease activity. In some embodiments, the kit contains a nucleic acid polymerase enzyme with reverse transcriptase activity. In some embodiments, the kit contains a nucleic acid polymerase enzyme having 5' to 3' exonuclease activity and reverse transcriptase activity. In some embodiments, the nucleic acid polymerase is a DNA polymerase.

In yet another aspect, the present disclosure provides a method of manufacturing a composition of magnetic beads described herein, comprising the steps of:
  a. contacting a stabilizer and nanoparticles from any one material selected from the group consisting of metals, metal salts, metal carbides, metal nitrides, metal sulfides, metal phosphides, metal oxides, or metal chelates comprising at least one transition metal under solvothermal conditions to form aggregates of controlled size of above 100 nm to form a magnetic core which is superparamagnetic; and
  b. coating the magnetic core formed in step (a) with a liquid glass.

In some embodiments, the diameter of the coated magnetic bead is between about 80-500 nm, more specifically between about 150-450 nm, more specifically between about 200-400 nm, and even more specifically between about 250-400 nm. In certain embodiments, the magnetic bead has a particle size of between 200-400 nm. In some embodiments, the diameter of the magnetic core is between about 50-450 nm, more specifically between about 100-400 nm, more specifically between about 150-350 nm, more specifically about 200-350 nm. In particular embodiments, the magnetic core is between about 250-320 nm, more specifically between about 260-300 nm, more specifically between about 270-290 nm. In some embodiments, the stabilizer is selected from the group consisting of citrate, histidine, cetyltrimethylammonium bromide (CTAB), cetyltrimethylammonium chloride (CTAC), sodium oleate, and polyacrylic acid. In a particular embodiment, the stabilizer is sodium citrate. In some embodiments, the magnetic core is $Fe_3O_4$, $\alpha\text{-}Fe_2O_3$, $\gamma\text{-}Fe_2O_3$, $MnFe_xO_y$, $CoFe_xO_y$, $NiFe_xO_y$, $CuFe_xO_y$, $ZnFe_xO_y$, $CdFe_xO_y$, $BaFe_xO$ and $SrFe_xO$, wherein x and y vary depending on the method of synthesis, and wherein x is preferably an integer of from 1 to 3 inclusive, more preferably 2, and wherein y is preferably 3 or 4 most preferably, $Fe_3O_4$. In particular embodiments the magnetic core is a magnetite core. In some embodiments, solvothermal conditions are conditions including 190-250° C. and increased pressure of 1-20 bar. In some embodiments, the magnetic beads are substantially spherical. In some embodiments, the liquid-glass coating comprises a silicate. In particular embodiments the silicate is selected from the group consisting of sodium silicate, potassium silicate, calcium silicate, lithium silicate, and magnesium silicate. In some embodiments, the silicate is sodium silicate. In some embodiments, the liquid-glass coating has a thickness of 20 nm or less. In certain embodiments, the liquid-glass coating has a thickness of 10 nm or less. In some embodiments step a. includes reducing a metal salt in the presence of a stabilizer. In certain embodiments, the metal salt is $FeCl_3$ and the stabilizer is sodium citrate to form a magnetite core. In certain embodiments, the liquid glass is sodium silicate. In certain embodiments, the method comprises the steps of:

a. forming a magnetite core by reducing $FeCl_3$ in the presence of sodium acetate, sodium citrate, and ethylene glycol at an elevated temperature for up to 18 hours;

b. coating the magnetite core formed in step (a) with a liquid glass, preferably sodium silicate.

BRIEF DESCRIPTION OF THE FIGURES

FIG. 3B illustrates the liquid glass coating reaction.

FIGS. 4A-4C include comparative SEM analyses showing the influence of reagent concentrations on the morphology of the MGPs described herein. FIG. 4A: Scale factor 1 (MC13); FIG. 4B: Scale factor 2 (MC15); FIG. 4C: Scale factor 4 (MC06).

DETAILED DESCRIPTION

Definitions

Figure 1A:
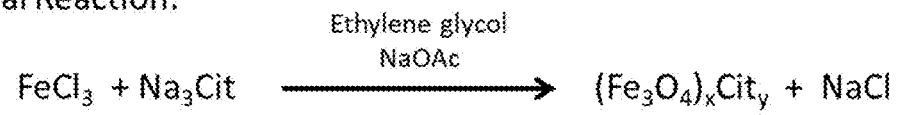
FIG. 1A illustrates a solvothermal reaction that may be used to generate the magnetite core of the particles described herein.

Unless otherwise defined herein, scientific and technical terms used herein have the meanings that are commonly understood by those of ordinary skill in the art. Further, unless otherwise required by context, singular terms include pluralities and plural terms include the singular. The articles "a" and "an" are used herein to refer to one or to more than one (i.e., to at least one) of the grammatical object of the article. By way of example, "an element" means one element or more than one element.

The terms "detect," "detecting," "detection," and similar terms are used in this application to broadly refer to a process or discovering or determining the presence or an absence, as well as a degree, quantity, or level, or probability of occurrence of something. For example, the term "detecting", when used in reference to a target nucleic acid sequence, can denote discovery or determination of the presence, absence, level or quantity, as well as a probability or likelihood of the presence or absence of the sequence. It is to be understood that the expressions "detecting presence or absence," "detection of presence or absence" and related expressions include qualitative and quantitative detection.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non-naturally occurring, and modified nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

The term "sample" or "biological sample" refers to any composition containing or presumed to contain nucleic acid from an individual. The term includes purified or separated components of cells, tissues, or blood, e.g., DNA, RNA, proteins, cell-free portions, or cell lysates. In one embodiment, the sample is a whole blood sample. As used herein, a "whole blood sample" includes blood drawn from the body from which no constituent, such as plasma or platelets, has been removed. Generally, the sample is unmodified except for the presence of an anticoagulant. A sample can also refer to other types of biological samples, e.g., plasma, serum, blood components (buffy coat), and dried blood spots. Samples also may include constituents and components of in vitro cultures of cells obtained from an individual, including cell lines. Specific additional examples of biological samples include feces, mucosal swabs, tissue aspirates, tissue homogenates, cell cultures and cell culture supernatants (including cultures of eukaryotic and prokaryotic cells), urine, saliva, sputum, and cerebrospinal sample.

"Solvothermal" conditions are applied in a solvothermal synthesis method of producing chemical compounds. Herein, solvothermal synthesis allows for the precise control over the size, shape distribution, and crystallinity of metal oxide nanoparticles or nanostructures. These characteristics can be altered by changing certain experimental parameters, including reaction temperature, reaction time, solvent type, surfactant type, and precursor type (R. Xu et al., Modern Inorganic Synthetic Chemistry, Elsevier, 2011, Amsterdam, pp. 63).

The term "ferrimagnetic" as used herein refers to a material consisting of populations of atoms with opposing but unequally distributed magnetic moments, thus resulting in a magnetic saturation and remanence once an external magnetic field is applied.

The term "paramagnetic" refers to a form of magnetism whereby certain materials are weakly attracted by an externally applied magnetic field, and form internal, induced magnetic fields in the direction of the applied magnetic field. Paramagnetism occurs due to the presence of unpaired electrons in the material, so all atoms with incompletely filled atomic orbitals are paramagnetic. Due to their spin, unpaired electrons have a magnetic dipole moment and act like tiny magnets. An external magnetic field causes the electrons' spins to align parallel to the field, causing a net attraction. Paramagnetic materials include aluminium, oxygen, titanium, and iron oxide (FeO). Notably, paramagnets do not retain any magnetization in the absence of an externally applied magnetic field because thermal motion randomizes the spin orientations. Consequently, the total magnetization drops to zero when the applied field is removed.

The term "superparamagnetic" refers to a form of magnetism which appears in small ferromagnetic or ferrimagnetic nanoparticles. In the absence of an external magnetic field the magnetization of the nanoparticles appears to be in average zero. This state is understood to be in the superparamagnetic state. In this state, an external magnetic field is able to magnetize the nanoparticles with the magnetic susceptibility of the superparamagnetic particles being much larger than that of paramagnetic particles.

Magnetic Particles

The problem to be solved by the present disclosure can be seen as providing magnetic particles with improved properties for sample preparation and for biological assays, in particular for automated processes that are conducted in a sample processing tubule. Systems that use a sample processing tubule, such as those described in the COBAS® LIAT® System (Roche Molecular Systems, Pleasanton, Calif.), have very challenging requirements for the magnetic particles. In such systems washing, incubation and elution steps happen not within several minutes but rather within a few seconds, thereby increasing the demands on the particles. In particular, the particles should provide for a strong magnetic response, should have a small particle size and should show a low remanent magnetization. In some aspects it was shown to be beneficial that the particles are superparamagnetic and have a size of >200 nm as otherwise the particles separate too slowly.

The solution to this problem is provided by the particles according to the present disclosure, which exhibit the desired properties of low magnetic remanence and fast magnetic separation times, high and quick binding capacities for nucleic acids with fast elution properties of the nucleic acids. Particularly, particles according to the present disclosure provide for an available surface area which is relatively high (for high and quick binding capacities), for a low coating thickness (for magnetic saturation), for a particle size which is approximately greater than 100 nm (for fast magnetic separation times), and for a magnetic core that is superparamagnetic (for low magnetic remanence).

In one aspect, the disclosure provides a magnetic particle or magnetic bead comprising a magnetic core produced under solvothermal conditions and a liquid glass-based coating, wherein the magnetic particle or magnetic bead is superparamagnetic. More specifically, the present disclosure provides a composition of magnetic particles. As used herein, "particles" (or "beads") refers to solid materials having a relatively small diameter. The particles contemplated herein are a solid dispersion of small magnetic cores with a liquid glass based coating. The particles are comparatively small and are substantially spherical. It should be noted that the terms "particles" and "beads" as well as "magnetic particles" and "magnetic beads" may be used interchangeably. The advantages of such particles or beads include, but are not limited to:

increased particle size, e.g., greater than 100 nm, such as, e.g., 100-500 nm, more specifically 200-400 nm providing a good balance between fast magnetic separation times, slow sedimentation times and increased outer surface area;

narrow particle size distributions yielding homogenous and reproducible results;

use of a superparamagnetic particle yielding low magnetic remanence and giving no tendency for agglomeration after introducing a magnetic force;

use of a relatively thin liquid glass coating leading to high saturation magnetization;

ease of manufacturability and process scalability; and optimized synthesis for the magnetite core and the coating reducing manufacturing time and cost of goods, with reduced waste.

Herein, it is to be noted that size is not the only deciding factor for magnetic properties of the particles. For example, iron oxides, such as $Fe_3O_4$, can be present in different modifications having different properties. In particular, the size of the crystallites can be relevant to the magnetic properties of the particles. For example, small crystallites may show significantly lower magnetic remanence and thus provide for superparamagnetic properties, whereas crystallites with a size of 200 nm or more may not exhibit superparamagnetic properties. In one specific embodiment, the magnetic core of the particles according to the disclosure are made up of small crystallites (e.g., a defined aggregate of magnetic nanoparticles further comprising a stabilizer). Thus, the particles according to the disclosure reach sizes of 100-500 nm, more specifically 200-400 nm, but still exhibit superparamagnetic properties. Moreover, the superparamagnetic properties can be decisive for the technical application as the particles may not agglomerate if they come into contact with a magnet several times.

One aspect of the disclosure is a composition of magnetic particles which are substantially spherical and have a small diameter and contain at least one magnetic object with a diameter greater than 100 nm. In certain aspects the diameter is between about 80-500 nm, more specifically between about 150-450 nm, more specifically between about 200-400 nm, and even more specifically between about 250-400 nm. In certain aspects the diameter of the magnetic core is between about 50-450 nm, more specifically between about 100-400 nm, more specifically between about 150-350 nm, more specifically about 200-350 nm. In particular aspects the magnetic core is between about 250-320 nm, more specifically between about 260-300 nm, more specifically between about 270-290 nm. The magnetic particles according to the present disclosure are glass droplets in which very small non-aggregating magnetic objects are dispersed. Hence, the magnetic particles described herein may also be referred to as "magnetic glass particles" ("MGPs"). Those objects that are referred to as magnetic are drawn to a magnet, i.e., ferromagnetic or superparamagnetic materials. Ferromagnetic materials can include materials that have not yet been premagnetized. Premagnetization in this context is understood to mean bringing in contact with a magnet, which increases the remanence. More specifically, the magnetic core of the magnetic particles according to the disclosure is superparamagnetic. Suitable materials for generating superparamagnetic beads are metals, metal salts, metal carbides, metal nitrides, metal sulfides, metal phosphides, metal oxides, or metal chelates comprising at least one transition metal. Preferred transition metals according to the disclosure include, but are not limited to, chromium, manganese, iron, cobalt, nickel, zinc, cadmium, nickel, gadolinium, copper, and molybdenum. More preferably, the metal, metal carbide, metal nitride, metal sulfide, metal phosphide, metal oxide, or metal chelate comprises at least iron. More preferably, the magnetic core comprises an iron oxide, in particular an iron oxide selected from the group consisting of $Fe_3O_4$, $\alpha$-$Fe_2O_3$, $\gamma$-$Fe_2O_3$, $MnFe_xO_y$, $CoFe_xO_y$, $NiFe_xO_y$, $CuFe_xO_y$, $ZnFe_xO_y$, $CdFe_xO_y$, $BaFe_xO$ and $SrFe_xO$, wherein x and y vary depending on the method of synthesis, and wherein x is preferably an integer of from 1 to 3 inclusive, more preferably 2, and wherein y is preferably 3 or 4. Most preferably, the magnetic core comprises $Fe_3O_4$. More specifically, preferred magnetic materials are iron or iron oxide, e.g., magnetite ($Fe_3O_4$), or $Fe_2O_3$.

According to the present disclosure the magnetic core material specified above comprises a defined aggregate of magnetic nanoparticles with a stabilizer. Suitable stabilizers are selected from at least one member of the group consisting of dicarboxylic acids, tricarboxylic acids, polyacrylic acid, amino acids, surfactants and fatty acids, including the salts and derivatives, such as esters and polymers, of the mentioned compounds. It is to thus be understood that the aforementioned group includes salts and derivatives, such as esters and polymers, of the mentioned compounds. Thus, the stabilizer is preferably selected from at least one member of the group consisting of dicarboxylic acids, dicarboxylic acid salts, dicarboxylic acid derivatives, tricarboxylic acids, tricarboxylic acid salts, tricarboxylic derivatives, polyacrylic acid, polyacrylic acid salts, polyacrylic acid derivatives, amino acids, amino acid salts, amino acid derivatives, surfactants, salt of surfactants, fatty acids, fatty acid salts and fatty acid derivatives. In one aspect, the stabilizer, such as citrate, is added in-situ during the formation of particle aggregates (the so-called supraparticles) forming the magnetic core of the particles according to the disclosure exhibiting the superparamagnetic properties. Herein, subsequent addition of the stabilizer after particle aggregate formation will not provide for the same result.

Preferably as fatty acids, fatty acid salts or fatty acid derivatives, such compounds are chosen which are capable of binding to the surface of the supraparticle, thereby stabilizing the supraparticle. A fatty acid employed as stabilizer is preferably a single chain of alkyl groups containing from 8 to 22 carbon atoms with a terminal carboxyl group (—COOH) and high affinity adsorption (e.g., chemisorption or physical adsorption) to the surface of the magnetic particle. The fatty acid has multiple functions including protecting the magnetic particle core from oxidation and/or hydrolysis in the presence of water, which can significantly reduce the magnetization of the nanoparticle (Hutten, et al. (2004) J. Bio-tech. 112:47-63); stabilizing the nanoparticle core; and the like. The term "fatty acid" includes saturated or unsaturated, and in particular unsaturated fatty acids. Exemplary saturated fatty acids include lauric acid, myristic acid, palmitic acid, stearic acid, arachidic acid, propionic acid, butyric acid, valeric acid, caproic acid, enanthic acid, caprylic acid, pelargonic acid, capric acid, undecylic acid, tridecylic acid, pentadecylic acid, margaric acid, nonadecylic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid and octatriacontanoic acid and the like. Exemplary unsaturated fatty acids include oleic acid, linoleic acid, linolenic acid, arachidonic acid, hexadecatrienoic acid, stearidonic acid, eicosatienoic acid, eicosatetraenoic acid, eicosapentaenoic acid, heneicosapentaenoic acid, docosapentaenoic acid, clupanodonic acid, docosahexaenoic acid, tetracosapentaenoic acid, tetracosahexaenoic acid, calendic acid, eicosadienoic acid, docosadienoic acid, adrenic acid, docosapentaenoic acid, tetracosatetraenoic acid, tetracosapentaenoic acid, 5-dodecenoic acid, 7-tetradecenoic acid, palmitoleic acid, vaccenic acid, paullinic acid, 15-docosenoic acid, 17-tetracosenoic acid, elaidic acid, gondoic acid, mead acid, erucic acid, nervonic acid, rumenic acid, calendic acid, jacaric acid, eleostearic acid, catalpic acid, punicic acid, rumelenic acid, parinaric acid, bosseopentaenoic acid, pinolenic acid, podocarpic acid and the like. The fatty acid can be synthetic or isolated from a natural source using established methods. Moreover, a fatty acid can be a derivative such as a fatty acid enol ester (i.e., a fatty acid reacted with the enolic form of acetone), a fatty ester (i.e., a fatty acid with the active hydrogen replaced by the alkyl group of a monohydric alcohol), a fatty amine or fatty amide, or in particular embodiments, a fatty alcohol as described above. A particularly preferred fatty acid is oleic acid.

A surfactant, as used in the context of the instant disclosure, is an organic compound that is amphipathic, i.e., containing both hydrophobic groups and hydrophilic groups. Preferably surfactants are chosen which are capable of binding to the surface of the supraparticle, thereby preferably stabilizing the supraparticle. Surfactants with a variety of chain lengths, hydrophilic-lipophilic balance (HLB) values and surfaces charges can be employed depending upon the application. Preferably, the surfactant according to the disclosure is a quateranary ammonium salt, alkylbenzenesulfonate, lignin sulfonate, polyoxylethoxylate, or sulfate ester. Non-limiting examples of surfactants are cetyltrimethylammonium bromide (CTAB), cetyltrimethylammonium chloride (CTAC), nonyphenolpolyethoxylates (i.e. NP-4, NP-40 and NP-7), sodium dodecylbenzenesulfonate, ammonium lauryl sulfate, sodium laureth sulfate, sodium myreth sulfate, docusate, perfluorooctanesulfonate, perfluorobutanesulfonate, alkylaryl ether phosphates, alkyl ether phosphates, sodium stearate, 2-acrylamido-2-methylpropane sulfonic acid, ammonium perfluorononanoate, magnesium laureth sulfate, perfluorononanoic acid, perfluorooctanoic acid, phospholipids, potassium lauryl sulfate, sodium alkyl sulfate, sodium dodecyl sulfate, sodium laurate, sodium lauroyl sarcosinate, sodium nonanoyloxybenzenesulfonate, sodium pareth sulfate, behentrimonium chloride, benzalkonium chloride, benzethonium chloride, bronidox, dimethyldioctadecylammonium bromide, dimethyldioctadecylammonium chloride, lauryl methyl gluceth-10 hydroxypropyl dimonium chloride, octenidine dihydrochloride, olaflur, N-oleyl-1,3-propanediamine, stearalkonium chloride, tetramethylammonium hydroxide, thonzonium bromide, cetomacrogol 1000, cetostearyl alcohol, cetyl alcohol, cocamide DEA, cocamide MEA, decyl polyglucose, disodium cocoamphodiacetate, glycerol monostearate, polyethylene glycol isocetyl ether, octylphenoxypolyethoxyethanol, lauryl gluco side, malto sides, monolaurin, mycosubtilin, nonoxynols, octaethylene glycol monododecyl ether, N-octyl beta-D-thioglucopyrano side, octyl gluco side, oleyl alcohol, pentaethylene glycol mono-dodecyl ether, polidocanol, poloxamer, polyethoxylated tallow amine, polyglycerol polyricinoleate, polysorbate, sorbitan, sorbitan monolaurate, sorbitan monostearate, sorbitan tristearate, stearyl alcohol, surfactin, Triton X-100, Tween 80, cocamidopropyl betaine, cocamidopropyl hydroxysultaine, dipalmitoylphosphatidylcholine, hydroxysultaine, lauryldimethylamine oxide, lecithin, myristamine oxide, peptitergents, sodium lauroamphoacetate and bis(2-ethylhexyl) sulfosuccinic ester.

The term "amino acids" as used within the meaning of the present disclosure refers to natural or unnatural amino acids or amino acid derivatives as well as to salts of amino acids. Preferably, amino acids are chosen which are capable of binding to the surface of the supraparticle thereby preferably stabilizing the supraparticle. Exemplary amino acids include cysteine, methionine, histidine, alanine, arginine, asparagine, aspartic acid, glutamic acid, glutamine, glycine, isoleucine, leucine, lysine, phenylalanine, proline, serine, threonine, tryptophan, tyrosine, valine, selenocysteine, pyrrolysine, cysteine, dehydroalanine, enduracididine, lanthionine, norvaline and derivatives thereof.

The term "dicarboxylic acid" within the meaning of the present disclosure refers to a hydrocarbon or substituted hydrocarbon containing two carboxylic acid functional groups (i.e., $R_1$—$(C(O)OH)_2$), where $R_1$ is (a) a linear hydrocarbon containing from 0-18 carbon units or (b) a cyclic hydrocarbon containing 3-8 carbon units, either as aromatic or non-aromatic rings. The term includes salts and derivatives of fatty acids, such as esters of fatty acids. Representative dicarboxylic acids are e.g. propanedioic acid, butanedioic acid, pentanedioic acid, hexanedioic acid, heptanedioic acid, octanedioic acid, nonanedioic acid, decanedioic acid, undecanedioic acid, dodecanedioic acid, hexadecanedioic acid, maleic acid, fumaric acid, glutaconic acid, traumatic acid, muconic acid, glutinic acid, citraconic acid, mesaconic acid, malic acid, aspartic acid, glutamic acid, tartronic acid, tartaric acid, diaminopimelic acid, saccharic acid, mesoxalic acid, oxaloacetic acid, acetonedicarboxylic acid, arabinaric acid, phthalic acid, isophthalic acid, terephthalic acid, diphenic acid, 2,6-naphthalenedicarboxylic acid.

The term "tricarboxylic acid" within the meaning of the present disclosure refers to a hydrocarbon or substituted hydrocarbon containing three carboxylic acid functional groups (i.e., $R_1$—$(C(O)OH)_3$), where $R_1$ is (a) a linear hydrocarbon containing from 3-18 carbon units or (b) a cyclic hydrocarbon containing 3-8 carbon units, either as aromatic or non-aromatic rings. The term includes salts and derivatives of fatty acids, such as esters of fatty acids. Representative tricarboxylic acids are e.g. citric acid (2-hydroxypropane-1,2,3 tri-carboxylic acid), isocitric acid (1-hydroxypropane-1,2,3 tricarboxylic acid), aconitic acid (prop-1-ene-1,2,3 tricarboxylic acid), propane-1,2,3-tricarboxylic acid, trimellitic acid (benzene-1,2,4-tricarboxylic acid), trimesic acid (benzene-1,3,5-tricarboxylic acid), oxalosuccinic acid (1-oxopropane-1,2,3-tricarboxylic acid) or hemimellitic acid (benzene-1,2,3-tricarboxylic acid). Preferably, the tricarboxylic acid is citric acid including citrates, i.e. salts and derivatives of citric acid.

Preferably, the stabilizer is selected from the group consisting of citric acid, histidine, cetyltrimethylammonium bromide (CTAB), cetyltrimethylammonium chloride (CTAC), sodium oleate, polyacrylic acid or mixtures of two or more thereof including the respective salts or derivatives thereof. Thus, the present disclosure also relates to a magnetic particle as described above, wherein the magnetic core preferably consists of a supraparticle consisting of aggregated magnetic nanoparticles with at least one stabilizer, wherein the at least one stabilizer is selected from the group consisting of citrate, histidine, cetyltrimethylammonium bromide (CTAB), cetyltrimethylammonium chloride (CTAC), sodium oleate, polyacrylic acid or mixtures of two or more thereof. In a particular embodiment, the stabilizer is sodium citrate.

Preferably the amount of stabilizer is in the range of from 1 to 80% by weight, more preferably in the range of from 5 to 70% by weight, more preferably in the range of from 10 to 50% by weight, most preferably 20 to 40% based on the total weight of the sum of stabilizer and the supraparticle.

In certain aspects, the magnetic core of the MGPs is produced under solvothermal conditions. Solvothermal conditions are to be understood to include about 190-250° C. and increased pressure of about 1-20 bar.

Also provided is a suspension of magnetic beads, e.g., which can be produced by adding a liquid to a composition of the MGPs and the suspension is mixed to homogeneity. A liquid that can be used in the suspension may include any liquid which does not affect the stability of the magnetic particles and may be used to produce a homogenous suspension. Suitable liquids are used which are suitable for processes in molecular biology, in particular deoxyribonucleic acid (DNA) or ribonucleic acid (RNA) purification processes which make use of the binding of these substances to glass particles under certain conditions. Alternative liquids comprise alcohols or any mixtures thereof with water or ketones. In one embodiment, a suspension can contain between 5 to 200 mg/mL MGPs. In other embodiments, suspension can contain between 5 to 100 mg/mL MGPs. In other embodiments, suspension can contain between 5 to 60 mg/mL MGPs. In certain embodiments, suspension can contain between 25 to 50 mg/mL MGPs.

Alternatively or additionally, the MGPs are suspended in aqueous buffered solutions which may optionally contain a chaotropic agent. Herein, the concentration may be between 2 and 8 mol/l, e.g., between 4 and 6 mol/l. Chaotropic salts can be sodium iodide, sodium perchlorate, guanidinium thiocyanate, guanidinium isothiocyanate or guanidinium hydrochlorite. A "chaotropic agent," as used herein, includes any chemical substance which will disturb the ordered structure of liquid water and will have the effect that DNA or RNA will bind to the MGPs if this agent is present in the DNA or RNA containing solution. Buffer systems which may be used for molecular biology purposes may be found e.g. in Sambrook et al. (1989), Molecular Cloning, Cold Spring Harbor University Press, New York, N.Y., USA. Preferred buffer substances are Tris-hydroxymethylamine (TRIS), phosphate, N-(2-Hydroxyethyl) piperazine-N'-(2-ethanesulfonic acid) (HEPES), salts thereof or other suitable substances. Additionally, substances may be present which modify the ionic strength of the solution, e.g., NaCl, KCl or $CaCl_2$ or which are metal cation complexing agents as e.g. ethylenediaminetetraacetic acid (EDTA) or the salts thereof. In another embodiment, the suspension of MGPs may additionally contain DNA or RNA optionally in a mixture with proteins, fatty acids, carbohydrates and other material from biological origin. In another embodiment the liquid may contain a mixture of one or more constituents selected from the group of alcohols, ketones, aqueous buffered solutions, chaotropic agents, substances which modify the ionic strength of the solution, complexing agents, biological material, DNA or RNA all with the features as described above.

Magnetic materials that can be used in the MGPs can be characterized by any suitable method known in the art. For example, magnetic saturation is the state reached when an increase in an applied external magnetic field cannot increase the magnetization of the material further, so the total magnetic flux density more or less levels off. Likewise, remanence or remanent magnetization or residual magnetism is the magnetization left behind in a ferromagnetic material (such as iron) after an external magnetic field is removed. In one embodiment, the MGPs contemplated herein have a saturation magnetization between 30-80 $Am^2/kg$, more specifically 50-70 $Am^2/kg$ and a magnetic remanence below 5 $Am^2/kg$, more specifically below 3, even more specifically below 2.

The magnetic core material used in the MGPs described herein includes a coating composed of an amorphous material containing a liquid glass coating, e.g., a sodium liquid glass coating. The uncoated magnetic core particles have a diameter of approximately 250-320 nm, more specifically 260-300 nm, more specifically 270-290 nm. After the liquid glass coating is applied, the coated bead has a diameter of approximately 270-340 nm, more specifically 280-320 nm, magnetized with 50-70 $Am^2/kg$, respectively.

Methods for Manufacturing Magnetic Particles

Further disclosed herein are methods of manufacturing a composition of magnetic beads disclosed above. Herein, in a first step a stabilizer is contacted with nanoparticles from any one material selected from the group consisting of metals, metal salts, metal carbides, metal nitrides, metal sulfides, metal phosphides, metal oxides, or metal chelates comprising at least one transition metal under solvothermal conditions. Thereby, aggregates of controlled size of above 100 nm are produced that form a magnetic core which is superparamagnetic. In a second step the magnetic core is coated with a liquid glass to form the magnetic beads according to the disclosure.

The reaction is performed under elevated temperature, preferably between 190-250° C., and elevated pressure, preferably 1-20 bar. Under such solvothermal conditions the stabilizer coordinates on the surface around the magnetic nanoparticles to give supraparticles. Hence, the magnetic core comprises a supraparticle consisting of aggregated, stabilizer-coated nanoparticles being aggregated with each other. Herein, the coating is a stabilizer which covers at least a part, preferably the whole surface, of each nanoparticle. Preferably, also in this case, each nanoparticle comprises a compound selected from the group consisting of metal, metal salts, metal carbide, metal nitride, metal sulfide, metal phosphide, metal oxide, metal chelate and a mixture of two or more thereof. It is to be understood that each nanoparticle present in the supraparticle may comprise a mixture of two or more of the above-mentioned group, i.e. two or more of a metal, metal salts, metal carbide, metal nitride, metal sulfide, metal phosphide, metal oxide, metal chelate and a mixture of two or more thereof. Further, mixtures of two or more different metals, two or more different metal salts, two or more different metal oxides, two or more different metal carbides, two or more different metal nitrides, two or more different metal sulphides, two or more different metal chelates or two or more different metal phosphides are conceivable. More preferably, each nanoparticle in the supraparticle comprises a metal oxide or a metal carbide. In a preferred embodiment, the metal is a transition metal. Preferred transition metals according to the disclosure include, but are not limited to, chromium, manganese, iron, cobalt, nickel, zinc, cadmium, nickel, gadolinium, copper, and molybdenum. Most preferably, the metal is iron. According to a particularly embodiment, each nanoparticle comprised in the supraparticle is a metal oxide nanoparticle, most preferably an iron oxide nanoparticle, in particular an $Fe_3O_4$ nanoparticle.

Thus, the present disclosure also relates to a magnetic particle as described above, as well as to a magnetic particle obtained or obtainable by the above described method, wherein the magnetic core comprises or preferably consists of a supraparticle consisting of aggregated nanoparticles wherein the nanoparticles are preferably being coated with at least one stabilizer.

Preferably, the magnetic core has a diameter in the range of from 80 to 500 nm, more specifically between about 150-450 nm, more specifically between about 200-400 nm, and even more specifically between about 250-400 nm. In certain embodiments, the magnetic bead has a particle size of between 200-400 nm. In some embodiments, the diameter of the magnetic core is between about 50-450 nm, more specifically between about 100-400 nm, more specifically between about 150-350 nm, more specifically about 200-350 nm. In particular embodiments, the magnetic core is between about 250-320 nm, more specifically between about 260-300 nm, more specifically between about 270-290 nm.

Preferably, the stabilizer is selected from at least one member of the group consisting of dicarboxylic acids, tricarboxylic acids, polyacrylic acid, amino acids, surfactants and fatty acids. It is to thus be understood that the aforementioned group includes salts and derivatives, such as esters and polymers, of the mentioned compounds. Thus, the stabilizer is preferably selected from at least one member of the group consisting of dicarboxylic acids, dicarboxylic acid salts, dicarboxylic acid derivatives, tricarboxylic acids, tricarboxylic acid salts, tricarboxylic derivatives, polyacrylic acid, polyacrylic acid salts, polyacrylic acid derivatives, amino acids, amino acid salts, amino acid derivatives, surfactants, salt of surfactants, fatty acids, fatty acid salts and fatty acid derivatives.

As used herein, the terms "coated" or "coating" are used to refer to the process of adsorption, van der Waals and/or non-polar group interactions (e.g., chemisorption or physical adsorption), or covalent binding of the magnetic nanoparticle and the stabilizer.

Figure 1B:
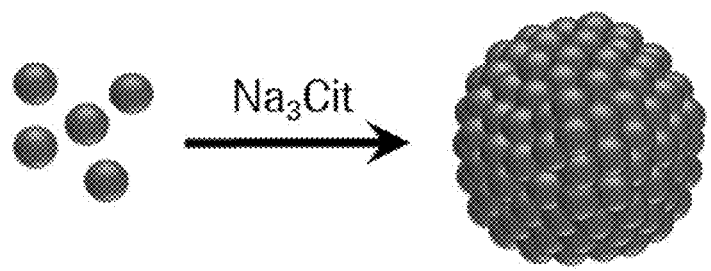
FIG. 1B further illustrates the addition of a stabilizer to the magnetite core. Preferably, citrate coordinates around magnetite nanoparticles to give supraparticles.

In a particular embodiment shown in FIG. 1A an iron(III) salt is reduced to $Fe_3O_4$ under solvothermal conditions to form magnetic nanoparticles. The reducing agent may be selected from the group of alcohols, preferably polyalcohols, such as ethylene glycol, diethylene glycol, triethylene glycol. Moreover, a stabilizer is present in the reaction mixture. As shown in FIG. 1B the stabilizer, such as natrium citrate, coordinates on the surface around the magnetic nanoparticles provides for the in situ formation of aggregates of nanoparticles with controlled sizes to form so called supraparticles.

Figure 3A:
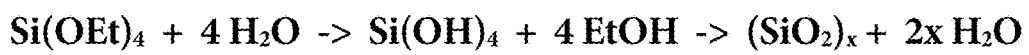
FIG. 3A illustrates the Tetraethyl Ortho Silicate (TEOS) coating reaction.

In a second step the supraparticles are coated with a coating selected from the group consisting of silica, silicates, silanes, and mixtures of two or more thereof. A method known in the art is the use of tetraethyl orthosilicate (TEOS) according to the Stober method (Stober et al., *J. Colloid Interface Sci.,* 1968, 26, 62). As shown in FIG. 3A the supraparticles are mixed with ethanol and $H_2O$ before TEOS is added. Stirring the mixture at a temperature of 15-35° C. for 8 to 24 hours provides magnetic beads covered with TEOS.

Further, the coating may be selected from the group of silica (e.g., tetraethyl orthosilicate, 3-(trimethoxysilyl) propyl methacrylate, vinyltrimethoxysilane, vinyltriethoxysilane, allyltri-methoxysilane, allyltriethoxysilane, triethoxyvinylsilane, 3-(trimethoxysilyl) propyl acrylate, trimethoxy(7-octen-1-yl)silane, trimethoxymethylsilane, triethoxymethylsilane, ethyltrimeth-oxysilane, triethoxy (ethyl) silane, trimethoxyphenylsilane, trimethoxy (2-phenylethyl) silane trimethoxy (propyl)silane, n-propyltriethoxysilane, isobutyl (trimethoxy) silane, isobutyltri-ethoxysilane) or the group of silicates (e.g. sodium silicate, potassium silicate, calcium silicate, lithium silicate, and magnesium silicate). As shown in FIG. 3B the superparticles may be subjected to a liquid glass ("LG") coating by mixing the superparticles with $H_2O$ and sodium liquid glass (e.g. sodium silicate) before adding HCl. Stirring the mixture at a temperature of 15-35° C. for 2 to 12 hours provides magnetic beads having a liquid glass coating. Depending on the efficacy of the coating the liquid glass coating step may be repeated at least once more. By slowly dripping and applying HCl to the solution it is possible to adjust the coating thickness exactly. Thus, extremely thin coatings may be obtained using clearly controlled conditions when adding HCl to the solution. As shown in the Example section below coatings that are too thick lead to impaired results, e.g., in the COBAS® LIAT® assays.

Assay Systems & Sample Processing Devices

The MGPs described herein can be used in any manual amplification assay method or in an automated nucleic acid amplification system or sample preparation system. In one embodiment, the MGPs can be used in any suitable commercially available PCR instrumentation and/or sample preparation system, including but not limited to, the COBAS® 6800/8800 System, COBAS® 4800 System, the COBAS® AmpliPrep Instrument, the COBAS® LIAT® System, the COBAS® p630 Instrument, the COBAS® s201 System, the COBAS® TAQMAN® 48 Analyzer, the COBAS® TAQMAN® Analyzer, the LIGHTCYCLER® 1536 System, the LIGHTCYCLER® 2.0 System, the LIGHTCYCLER® 480 System, the LIGHTCYCLER® 96 System, the MAGNA PURE® 96 System, the MAGNA PURE® Compact System, the MAGNA PURE® LC 2.0 System, or the FLOW Solution (all products of Roche Molecular Systems, Inc., Pleasanton, Calif. (see, e.g., www.molecular.roche.com/systems)).

In a specific embodiment, the MGPs described herein are used in a sample processing device configured to perform a nucleic acid amplification technique. Nucleic acids extracted from a biological sample may be further processed by amplifying the nucleic acids using any of the methods described hereinabove. In a specific embodiment, the nucleic acids extracted from the organism are RNA and their processing includes a coupled reverse transcription and polymerase chain reaction (RT-PCR) using combinations of enzymes such as Tth polymerase and Taq polymerase or reverse transcriptase and Taq polymerase. In some embodiments, nicked circular nucleic acid probes can be circularized using T4 DNA ligase or AMPLIGASE® DNA ligase (Roche Molecular Systems, Inc.) and guide nucleic acids, followed by detecting the formation of the closed circularized probes after an in vitro selection process. Such detection can be through PCR, TMA, RCA, LCR, NASBA or SDAR using enzymes known to those familiar with the art. In exemplary embodiments, the amplification of the nucleic acids can be detected in real time by using fluorescent-labeled nucleic acid probes or DNA intercalating dyes as well as a photometer or charge-coupled device in the molecular analyzer to detect the increase in fluorescence during the nucleic acid amplification. These fluorescently-labeled probes use detection schemes well known to those familiar in the art (i.e., TAQMAN® nucleic acid probes (Roche Molecular Systems, Inc.), molecular beacons, fluorescence resonance energy transfer (FRET) probes, SCORPION® probes (Qiagen Manchester Limited LLC, Manchester, UK) and generally use fluorescence quenching as well as the release of quenching or fluorescence energy transfer from one reporter to another to detect the synthesis or presence of specific nucleic acids. In one embodiment, the MGPs disclosed herein are used in a device comprising self-contained microscale to macroscale channels, chambers, reservoirs, detection and processing regions. The device can be a cartridge, device, container, or pouch, e.g., as described in U.S. Pat. Nos. 6,440,725; 6,783,934; 6,818,185; 6,979,424; 8,580,559; and 8,940,526, the disclosures of which are incorporated herein by reference in their entireties, as well as devices such as those available from Cepheid Corp., Idaho Technology, Inc., and/or Biofire Diagnostics, Inc.

For example, the device can be a self-contained nucleic acid analysis pouch which includes a cell lysis zone, a nucleic acid preparation zone, a first-stage amplification zone, a second-stage amplification zone, as shown in FIG. 1 of US Application Publication No. 201000056383, the disclosure of which is incorporated herein by reference. The pouch comprises a variety of channels and blisters of various sizes and is arranged such that the sample flows through the system and various zones and processed accordingly. Sample processing occurs in various blisters located within the pouch. Numerous channels are provided to move the sample within and between processing zones, while other channels are provided to deliver fluids and reagents to the sample or to remove such fluids and reagents from the sample. Liquid within the pouch is moved between blisters by pressure, e.g., pneumatic pressure. In this particular embodiment, the MGPs described herein are provided in a compartment configured to house the MGPs and in fluid communication with one or other channels and blisters such that the MGPs can be incorporated into the sample processing workflow and processed accordingly.

In an alternative example, the device can be a self-contained nucleic acid analysis cartridge as shown in FIGS. 3-5 and 9 of U.S. Pat. No. 9,322,052, which is incorporated herein by reference. The cartridge includes, inter alia, multiple chambers comprising a sample chamber for holding a fluid sample introduced through the inlet port, a wash chamber for holding a wash solution, a reagent chamber for holding a lysing reagent, a lysis chamber, a waste chamber for receiving used sample and wash solution, a neutralizer chamber for holding a neutralizer, and a master mix chamber for holding a master mix (e.g., amplification reagents and fluorescent probes) and for mixing the reagents and probes with analyte separated from the fluid sample, a reaction vessel, and a detection chamber. In this embodiment, the MGPs described herein are provided in a compartment configured to house the MGPs and in fluid communication with one or other channels and blisters such that the MGPs can be incorporated into the sample processing workflow and processed accordingly.

In a specific embodiment, the methods described herein are conducted in a sample processing device such as that described in U.S. Pat. No. 7,718,421, the disclosure of which is incorporated herein by reference. Segmented devices, such as those described in U.S. Pat. No. 7,718,421, provide a convenient vessel for receiving, storing, processing, and/or analyzing a biological sample. In certain embodiments, the segmented device facilitates sample processing protocols involving multiple processing steps. In certain embodiments, a sample may be collected in a sample device, and the device is then positioned in an analyzer which manipulates the device and its contents to process the sample.

A particular embodiment includes a flexible device which has been segmented into compartments by breakable seals. The individual segments may contain various reagents and buffers for processing a sample. Clamps and actuators may be applied to the device in various combinations and with various timings to direct the movement of fluid and to cause the breakable seals to burst. This bursting of the breakable seals may leave an inner device surface that is substantially free of obstructions to fluid flow. In one embodiment, the flow of the biological sample may be directed toward the distal end of the device as the processing progresses, while the flow of waste may be forced to move in the opposite direction, toward the opening of the device where the sample was initially input. This sample inlet can be sealed, possibly permanently, by a cap with a locking mechanism, and a waste chamber may be located in the cap to receive the waste for storage. A significant benefit of this approach is that the processed sample does not come into contact with surfaces that have been touched by the unprocessed sample. Consequently, trace amounts of reaction inhibitors present in the unprocessed sample that might coat the walls of the device are less likely to contaminate the processed sample.

Figure 5:
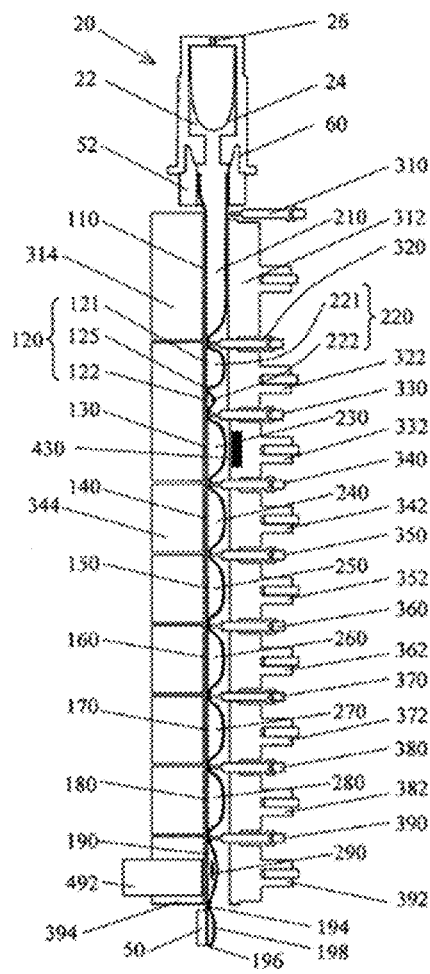
FIG. 5 illustrates a sample processing device that can be used with the beads described herein.

The sample processing device is shown in FIG. 5 and may include a transparent flexible device 10 capable of being configured into a plurality of segments, such as 16, 110, 120, 130, 140, 150, 160, 170, 180, and/or 190, and being substantially flattened by compression. In an embodiment, a device may have at least two segments. In an embodiment, a device may have at least three segments. The flexible device can provide operational functionality between approximately 2-105° C., compatibility with samples, targets and reagents, low gas permeability, minimal fluorescence properties, and/or resilience during repeated compression and flexure cycles. The device may be made of a variety of materials, examples of which include but are not limited to: polyolefins such as polypropylene or polyethylene, polyurethane, polyolefin co-polymers and/or other materials providing suitable characteristics.

In exemplary embodiments, one or more reagents can be stored either as dry substance and/or as liquid solutions in device segments. In embodiments where reagents may be stored in dry format, liquid solutions can be stored in adjoining segments to facilitate the reconstitution of the reagent solution. Examples of typical reagents include: lysis reagent, elution buffer, wash buffer, DNase inhibitor, RNase inhibitor, proteinase inhibitor, chelating agent, neutralizing reagent, chaotropic salt solution, detergent, surfactant, anticoagulant, germinant solution, isopropanol, ethanol solution, antibody, nucleic acid probes, peptide nucleic acid probes, and phosphothioate nucleic acid probes. In embodiments where one of the reagents is a chaotropic salt solution, a preferred component is guanidinium isocyanate or guanidinium hydrochloride or a combination thereof. In some embodiments, the order in which reagents may be stored in the device relative to the opening through which a sample is input, reflects the order in which the reagents can be used in methods utilizing the tube. In preferred embodiments, a reagent includes a substance capable of specific binding to a preselected component of a sample. For example, a substance may specifically bind to nucleic acid, or a nucleic acid probe may specifically bind to nucleic acids having particular base sequences.

A real-time detection of a signal from a device segment can be achieved by using a sensor, such as a photometer, a spectrometer, or a CCD, connected to a block. In exemplary embodiments, pressure can be applied by an actuator on the device segment to suitably define the device segment's shape. The format of signal can be an intensity of a light at certain wavelength, such as a fluorescent light, a spectrum, and/or an image, such as image of cells or manmade elements such as quantum dots. For fluorescence detection, an excitation of light from the optical system can be used to illuminate a reaction, and emission light can be detected by the photometer. To detect a plurality of signals having specific wavelengths, different wavelength signals can be detected in series or parallel by dedicated detection channels or a spectrometer.

Kits

In some embodiments, the MGPs and compositions and suspensions thereof described herein are included in a kit or a component thereof. The kits contemplated herein can include any manufacture (e.g., a package or a container), including at least one device for specifically amplifying, capturing, tagging/converting or detecting a target nucleic acid sequence as described herein, wherein the compositions described herein are included in the device or provided as a separate kit component, vial or container. The kit can further include instructions for use, supplemental reagents, control materials, and/or components or modules used in the amplification methods described herein or a step thereof. The kit can also include at least one of the following components: nucleoside triphosphates, nucleic acid polymerase, and buffers necessary for the function of the nucleic acid polymerase. One or more of the kit components can be included in the kit as separate components, e.g., in separate vials or containers packaged together, or one of more of the kit components can be included in the kit in the same vial or container.

Such kits may comprise components which can be used during a sample preparation procedure, e.g., microtiter plates in the 96- or 384-well format or ordinary reaction tubes manufactured, e.g., by Eppendorf, Hamburg, Germany and all other reagents for carrying out a nucleic acid amplification using the control materials described herein. The kit can include MGPs, as described herein. The kit can further or additionally comprise a protease reagent and a lysis buffer containing e.g. chaotropic agents, detergents or alcohols or mixtures thereof allowing for the lysis of cells. These components of the kit may be provided separately in tubes or storage containers. Depending on the nature of the components, these may be provided in a single tube or storage container. The kit may further or additionally comprise a washing solution which is suitable for the washing step of the magnetic glass particles when a nucleic acid is bound thereto. This washing solution may contain ethanol and/or chaotropic agents in a buffered solution or solutions with an acidic pH without ethanol and/or chaotropic agents as described above. Often the washing solution or other solutions are provided as stock solutions which have to be diluted before use.

The kit may further comprise an eluent or elution buffer, i.e. a solution or a buffer (e.g. 10 mM Tris, 1 mM EDTA, pH 8.0) or pure water to elute the nucleic acid bound to the magnetic glass particles. Further, additional reagents or buffered solutions may be present which can be used for the purification of a nucleic acid.

In a specific embodiment, the kit contains a polymerase enzyme having 5' to 3' exonuclease activity. The kit can also contain an enzyme with reverse transcriptase activity. In another embodiment, the kit contains a polymerase enzyme having 5' to 3' exonuclease activity and reverse transcriptase activity.

Methods and Uses of the Magnetic Particles

The MGPs (and compositions and suspensions thereof) described herein can be used to analyze any target nucleic acid, including but not limited to, nucleic acids associated with bacterial pathogens (e.g. methicillin resistant *Staphylococcus aureus, C. difficile*, tuberculosis, group B strep., sepsis, *chlamydia*, and gonorrhea), viral pathogens (e.g. influenza, HIV, HCV, and HBV), tumor cells (e.g., bladder cancer, lung cancer, breast cancer, colon cancer, and leukemia), chromosomal alterations, such as gene duplication, gene deletions or gene translocations, cells expressing specific cell surface markers such as CD4+ cells, detection of gene mutation/alterations such as single nucleotide polymorphisms (SNPs) and methylation status of genes.

In one embodiment, the MGPs can be used for assays that include nucleic acid capture, enrichment, analysis, and/or purification. For example, the MGPs described herein can be used to capture a target nucleic acid. Capturing can help to enrich the target nucleic acid and to remove reaction inhibitors from a sample. MGPs can be used for capture, enrichment, and/or purification under defined chemical and temperature conditions, and may release the components under different chemical and temperature conditions.

In a specific embodiment, the MGPs are used to analyze nucleic acids in a sample by nucleic acid amplification methods. Nucleic acid amplification methods may include but are not limited to, the Ligase Chain Reaction (LCR; Wu D. Y. and Wallace R. B., Genomics 4 (1989) 560-69; and Barany F., Proc. Natl. Acad. Sci. USA 88 (1991)189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808), and NASBA (U.S. Pat. No. 5,130,238). Further, the MGPs described herein can also be used in the following methods: strand displacement amplification (SDA), transcription mediated amplification (TMA), and Qb-amplification (for a review see e.g. Whelen A. C. and Persing D. H., Annu. Rev. Microbiol. 50(1996) 349-373; Abramson R. D. and Myers T. W., Curr Opin Biotechnol 4 (1993) 41-47).

One method of nucleic acid amplification is the Polymerase Chain Reaction (PCR) which is disclosed in U.S. Pat. Nos. 4,683,202, 4,683,195, 4,800,159, and 4,965,188, among other references. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the target nucleic acids. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating. A "thermostable polymerase" is a nucleic acid polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable nucleic acid polymerases have, for example, been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 5 sec to 9 min. In order to not expose the respective polymerase to such high temperatures for too long and thus risking a loss of functional enzyme, it is preferred to use short denaturation steps. In a specific embodiment, the denaturation step is up to 30 sec, e.g., up to 20 sec, up to 10 sec, up to 5 sec, and specifically, about 5 sec.

If the double-stranded template nucleic acid is denatured by heat, the reaction mixture is allowed to cool to a temperature that promotes annealing of each primer to its target sequence on the target nucleic acids. The temperature for annealing is preferably from about 35° C. to about 70° C., further preferably about 45° C. to about 65° C.; further preferably about 50° C. to about 60° C., further preferably about 55° C. to about 58° C. Annealing times can be from about 10 sec to about 1 min (e.g., about 20 sec to about 50 sec; about 30 sec to about 40 sec). In this context, it can be advantageous to use different annealing temperatures in order to increase the inclusivity of the respective assay. In brief, this means that at relatively low annealing temperatures, primers may also bind to targets having single mismatches, so variants of certain sequences can also be amplified. This can be desirable if e.g. a certain organism has known or unknown genetic variants which should also be detected. On the other hand, relatively high annealing temperatures bear the advantage of providing higher specificity, since at higher temperatures the probability of primer binding to not exactly matching target sequences continuously decreases. In order to benefit from both phenomena, in some embodiments of the disclosure it is preferred that the process described above comprises annealing at different temperatures, preferably first at a lower, then at a higher temperature. If, e.g., a first incubation takes place at 55° C. for about 5 cycles, non-exactly matching target sequences may be (pre-) amplified. This can be followed e.g. by about 45 cycles at 58° C., providing for higher specificity throughout the major part of the experiment. This way, potentially important genetic variants are not missed, while the specificity remains relatively high.

The reaction mixture is then adjusted to a temperature at which the activity of the polymerase is promoted or optimized, i.e., a temperature sufficient for extension to occur from the annealed primer to generate products complementary to the nucleic acid to be analyzed. The temperature should be sufficient to synthesize an extension product from each primer that is annealed to a nucleic acid template, but should not be so high as to denature an extension product from its complementary template (e.g., the temperature for extension generally ranges from about 40° to 80° C. (e.g., about 50° C. to about 70° C.; about 60° C.). Extension times can be from about 10 seconds to about 5 min, preferably about 15 sec to 2 min, further preferably about 20 sec to about 1 min, further preferably about 25 sec to about 35 sec. The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acids. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Example

Synthesis of Magnetic Core

Figure 2:
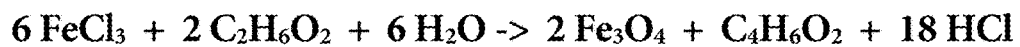
FIG. 2 illustrates the possible mechanism of a chemical reaction that may be used to produce the magnetite core of the particles described herein.
Figure 2:
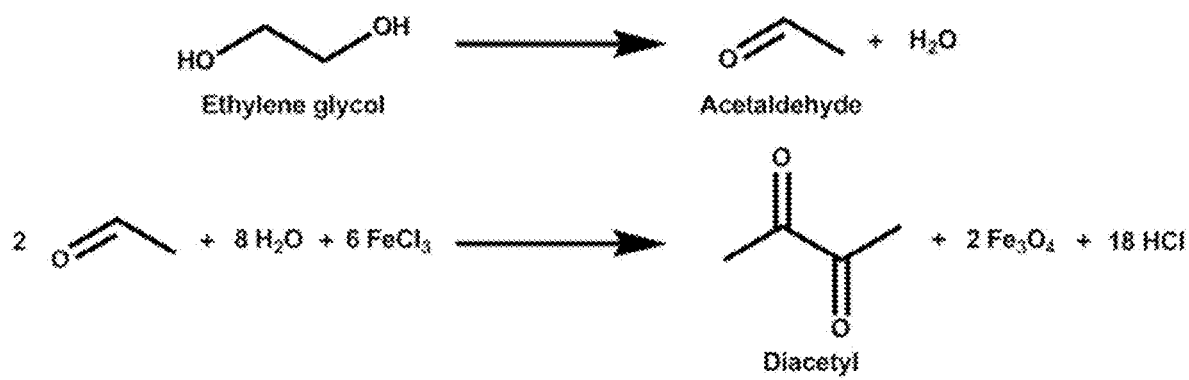

The magnetic core was synthesized by reducing iron(III) chloride to iron(II,III)oxide ($Fe_3O_4$) under solvothermal conditions as described in Liu et al. (Angew. Chem. Int. Ed., 2009, 48, 5875-5879). Briefly, the magnetic core ("MC-Beads") were produced by degassing 800 mL ethylene glycol with argon for 1 hour. $FeCl_3$ (44 g) was added and dissolved and the solution was transferred to a pressure reactor. Sodium citrate (9.7 g) and sodium acetate (51.9 g) were added and the mixture was heated to 160° C. for 1 hour, and then the temperature was raised to 200° C. and maintained for 18 hours. The mixture was subjected to magnetic washing using ethanol and water (3× ethanol, 3× water). The MC-beads obtained were superparamagnetic. The reaction schemes are shown in FIGS. 1A and 1B. Herein, sodium acetate was used as proton acceptor, while sodium citrate was added to promote the formation of defined nanoparticle aggregates as shown in FIG. 1B. The possible reduction mechanism is shown in FIG. 2.

Coating of Magnetic Core

One portion of the MC-Beads were coated with tetraethyl orthosilicate (TEOS) according to the Stober method (Stober et al., *J. Colloid Interface Sci.*, 1968, 26, 62) as follows: 0.4 g MC-Beads produced by the foregoing method, were mixed with 1280 mL ethanol, 312 mL $H_2O$, and 16 mL $NH_4OH$. The mixture was added to a flow-through US cell activated for 30 minutes. TEOS (2 mL) was added and the mixture was stirred at 25° C. for 16 hours. The mixture was subjected to magnetic washing using ethanol and water (3× ethanol, 3× water).

Another portion of the MC-Beads were subjected to a liquid glass ("LG") coating by mixing 0.5 g beads with 160 mL $H_2O$ and 40 mL sodium liquid glass in 250 mL glass reactor with a flow-through US cell (and pre-mixed for 10 minutes). HCl (1M, 66 mL) was added and the mixture was stirred continuously and subjected to a flow-through US cell for 2 hours. The mixture was then subjected to a magnetic wash (3× water), and the foregoing liquid glass coating steps were repeated at least once more. Exemplary beads are MC13-LG to MC17-LG.

Another portion of the MC-beads were subjected to a liquid glass ("LG") coating by mixing MC-beads (2-15 g/L) with various amounts of sodium liquid glass (38-100 mL) in a total volume of up to 250 mL in a glass reactor with a flow-through US cell (and pre-mixed for 10 minutes). HCl (1-3 M, 45-110 mL) was added dropwise and the mixture was stirred continuously and subjected to a flow-through US cell for 4-6 hours. The mixture was then subjected to a magnetic wash (3× water). Exemplary beads are MC47-LG and MC48-LG.

Results

The uncoated MC-Beads had a diameter of approximately 270 nm, the TEOS-coated particles had a diameter of about 400 nm, and the liquid glass coated particles had a diameter of about 280 nm, magnetized with 46.7 (TEOS) and 54 (LG) $Am^2/kg$, respectively. An overview of the experiments using the uncoated MC-Beads compared to the beads as synthesized according to the method laid out in Liu et al., is shown in Table 1.

TABLE 1

| | | | | | | | | |
|---|---|---|---|---|---|---|---|---|
| | Characterization of uncoated beads | | | | | | | |
| Name | $FeCl_3$ [mmol] | $Na_3Cit$ [Eq] | NaOAc [Eq] | EG [mL] | Yield [g] | Magn. [$Am^2$/kg] | Rem. [$Am^2$/kg] | Size [nm] |
| Lit[3] | 4 | 0.10 | 3.66 | 20 | n/a | n/a | n/a | 170 |
| Lit[3] | 4 | 0.17 | 3.66 | 20 | n/a | 73.6 | n/a | 250 |
| Lit[3] | 4 | 0.26 | 3.66 | 20 | n/a | n/a | n/a | 300 |
| MC01 | 163 | 0.23 | 3.89 | 800 | 13.8 | 59.7 | 0.03 | |
| MC05 | 563 | 0.27 | 4.49 | 650 | 37.5 | n/a | n/a | |
| MC06 | 650 | 0.23 | 3.89 | 600 | 54.5 | 72.3 | 11.2 | |
| MC13 | 163 | 0.23 | 3.89 | 800 | 13.3 | 56.7 | 0.80 | 295 |
| MC14 | 163 | 0.33 | 3.89 | 800 | 13.4 | 57.6 | 0.74 | 298 |
| MC15 | 326 | 0.23 | 3.89 | 700 | 23.9 | 68.2 | 1.93 | 302 |
| MC16 | 163 | 0.23 | 3.89 | 800 | 13.2 | 57.5 | 0.85 | 296 |
| MC17 | 163 | 0.23 | 3.89 | 800 | 12.2 | 56.1 | 0.65 | 353 |

Figure 4C:
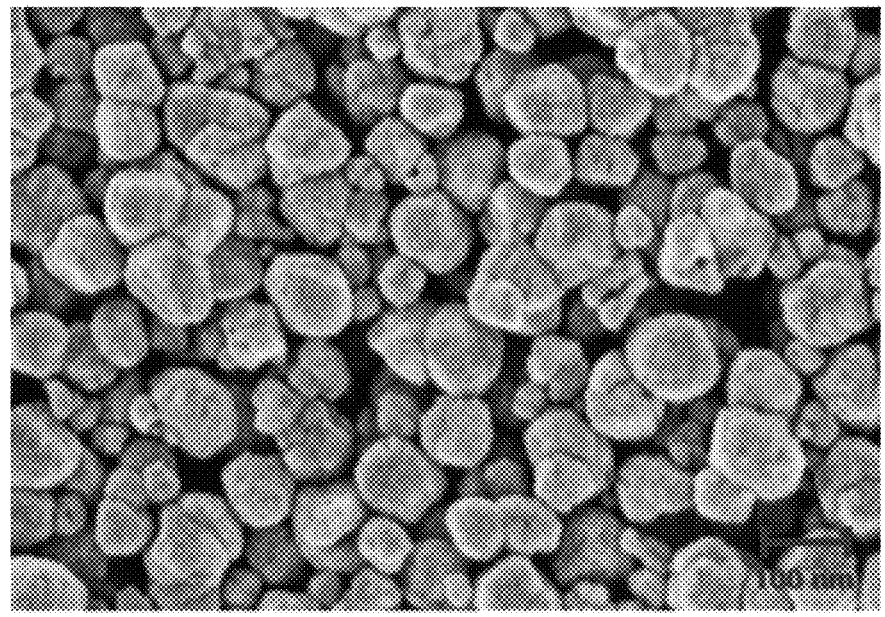

The yields of the higher concentrated reactions increased linearly. Additionally, an increase of the saturation magnetization ("Magn.") was observed. The magnetic remanence ("Rem.") increased as well. SEM analysis showed the influence of the reagent concentrations on the morphology of the nano MGPs, as illustrated in FIGS. 4A-C.

As outlined above the coating method was adapted from EP2916327B1. The reaction time was reduced from over two days to 4 hours and the ultrasonication procedure was optimized by using a bypass probe, which allowed easy scale up of the coating procedure and was shown by successfully coating a 10 gram batch, while in EP2916327B1 a 500 mg batch is used. For comparison, the magnetic cores were coated by the Stober method as well, where TEOS was used as reagent. Table 2 shows the different synthesis conditions.

TABLE 2

Characterization of coated beads

| Name | Amount magnetic particles [g] | Liquid glass [mL] | TEOS [mL] | Time [h] | Magn. [Am²/kg] | Rem. [Am²/kg] | Size [nm] |
|---|---|---|---|---|---|---|---|
| MC13LG1 | 0.5 | 120 | — | 22 | 54.0 | 0.96 | 308 |
| MC13LG3 | 1.5 | 240 | — | 4 | 53.7 | 0.74 | 298 |
| MC13TEOS3 | 0.4 | — | 7.5 | 16 | 41.7 | 0.44 | 306 |
| MC13TEOS5 | 0.4 | — | 2 | 16 | 46.7 | 0.49 | 300 |
| MC13TEOS6 | 0.4 | — | 1 | 16 | 43.8 | 0.47 | 312 |
| MC14LG1 | 0.5 | 80 | — | 4 | 50.5 | 0.61 | 318 |
| MC14TEOS1 | 0.4 | — | 2 | 16 | 43.4 | 0.47 | 353 |
| MC15LG1 | 1.5 | 240 | — | 4 | 64.6 | 2.00 | 300 |
| MC15LG1LG1 | 0.5 | 160 | — | 8 | 64.3 | 2.27 | 297 |
| MC16LG1 | 0.5 | 80 | — | 4 | 51.0 | 0.67 | 297 |
| MC16LG2 | 1.5 | 240 | — | 4 | 53.2 | 0.75 | 264 |
| MC16LG3 | 10 | 1600 | — | 4 | 53.1 | 0.79 | 303 |
| MC17LG1 | 0.5 | 80 | — | 4 | 52.7 | 0.74 | 320 |

In a third step, the functionality of the MGPs was demonstrated on the COBAS® LIAT® System. The COBAS® LIAT® System is a point-of-care system that fully automates sample preparation, PCR amplification and real-time detection of target DNA/RNA sequences on the COBAS® LIAT® Analyzer. The turn-around-time (TAT) is very rapid, ranging 10-20 minutes. The total time of nano-MGP nucleic acid binding, enriching and purification can be as short as 5 min or less. In these test, 10 µL of each nano-MGP preparation at 25 mg/mL concentrations were filled into COBAS® LIAT® tubes. Clostridium difficile (C. diff), Influenza type A (FluA), Influenza type B (FluB), and human Respiratory Syncytial Virus (RSV) were used as target nucleic acids. Low cycle threshold (Ct) values and high amplification (Amp) values are preferred. MC-LG beads showed consistent performance for detection of DNA or RNA targets from bacterial or viral organisms, while MC-TEOS showed delayed Ct values and low Amp values. The results for the functional performance of the MGPs are summarized in Table 3.

TABLE 3 functional performance of MGPs

| Name | C. diff Ct | C. diff Amp | FluA Ct | FluA Amp | FluB Ct | FluB Amp | RSV Ct | RSV Amp |
|---|---|---|---|---|---|---|---|---|
| MC13LG1 | 26.3 | 27.4 | 28.4 | 4.5 | 28.4 | 3.96 | 27.2 | 3.74 |
| MC13LG3 | 26.5 | 21.6 | — | — | — | — | — | — |
| MC13TEOS3 | 33.1 | 1.32 | — | — | — | — | — | — |
| MC13TEOS5 | 29.3 | 11.5 | 34.3 | 1.66 | 34.7 | 1.41 | — | — |
| MC13TEOS6 | 31.4 | 3.56 | 36.4 | 0.38 | 34.5 | 0.9 | 33.6 | 2.4 |
| MC14LG1 | 25.8 | 26.3 | 28.9 | 4.6 | 29.8 | 2.81 | 27 | 3.1 |
| MC14TEOS1 | 31.8 | 3.14 | 35.5 | 0.69 | 34.8 | 1.61 | 34.2 | 1.9 |
| MC15LG1 | 27.4 | 16.64 | 30 | 4.32 | 30 | 31.6 | 4.53 | 4.53 |
| MC15LG1LG1 | 26.9 | 17.8 | 30.1 | 4.51 | 30.1 | 31.8 | 4.93 | 4.93 |
| MC16LG1 | 26.5 | 30.1 | 28.9 | 4.71 | 28.4 | 3.71 | 31.1 | 1.4 |
| MC16LG2 | 27.2 | 17.5 | 29.8 | 4.4 | 29.4 | 4.3 | 31.2 | 2.7 |
| MC16LG3 | 26.2 | 21.4 | 29 | 3.97 | 28.9 | 2.54 | 31.1 | 0.95 |
| MC17LG1 | 26.5 | 29.1 | 28.9 | 4.99 | 28.8 | 3.82 | 31.4 | 1.54 |

Physical Properties of Coated Particles

MC47 and MC48 beads were subjected to a liquid glass ("LG") coating by mixing MC-beads (2-15 g/L) with various amounts of sodium liquid glass (38-100 mL) in a total volume of up to 250 mL in a glass reactor with a flow-through US cell (and pre-mixed for 10 minutes). HCl (1-3 M, 45-110 mL) was added dropwise depending on desired coating thickness and the mixture was stirred continuously and subjected to a flow-through US cell for 4-6 hours. The mixture was then subjected to a magnetic wash (3× water).

TABLE 4

Isoelectric point and silica coating of MGPs.

| Sample | Silica coating [wt %] | Isoelectric point |
|---|---|---|
| MC48 | 0 | 4.5 |
| MC48LG2 | 15 | 1.5 |
| MC48LG3 | 13 | 1.8 |
| MC48LG5 | 7 | 2.5 |
| MC48LG6 | 8 | 2.4 |
| MC48LG7 | 20 | 1.2 |
| MC48LG9 | 8 | 2.4 |

Figure 6:
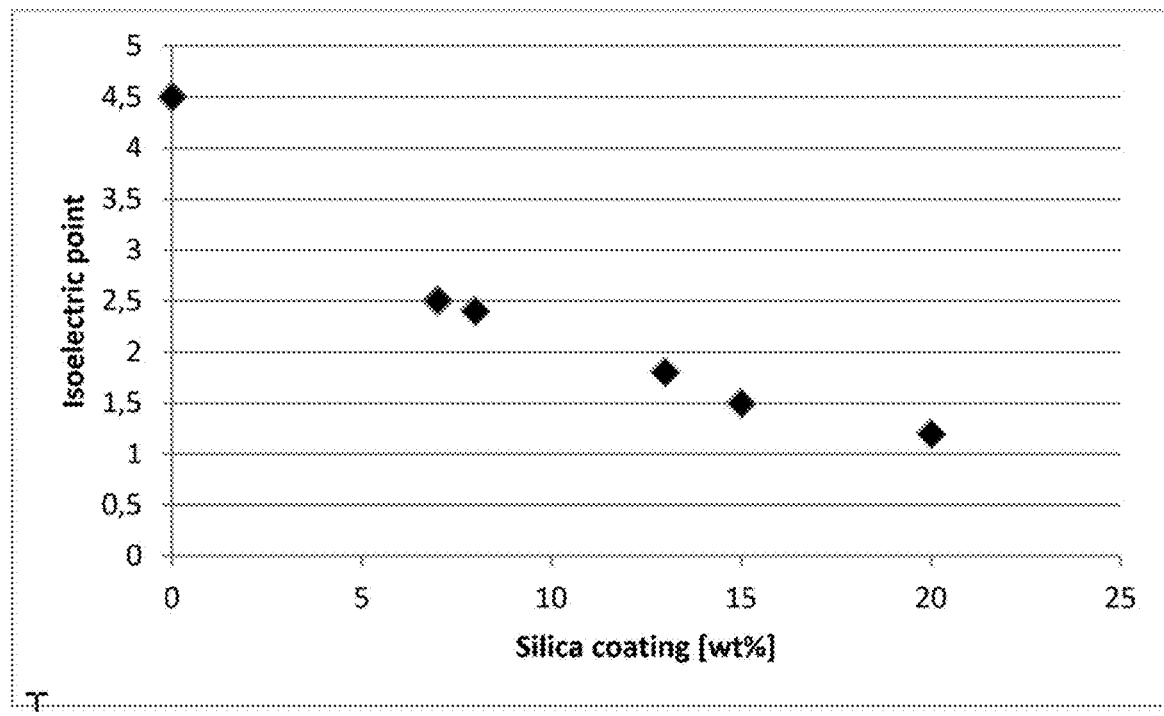
FIG. 6 illustrates the dependence of the isoelectric point of the particles (MC48 samples) on the silica coating thickness.

FIG. 6 and Table 4 show the dependence of the isoelectric point of the particles to the coating thickness (i.e., the silica content) of the particles. Herein, it is clearly shown, that with increasing silica coating the value of the isoelectric point is decreasing.

Figure 7A:
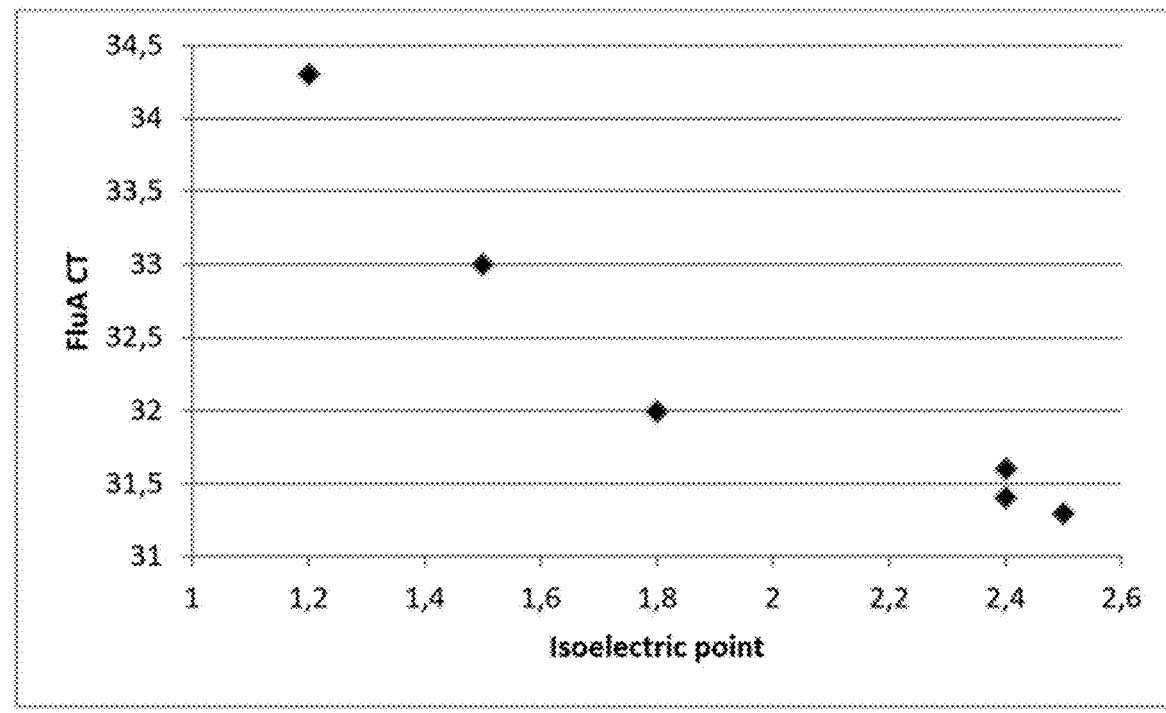
FIGS. 7A-7C illustrate the dependence of the measured FluA Ct values (FIG. 7A), FluB Ct values (FIG. 7B) and RSV Ct values (FIG. 7C) of the MC48 samples on their isoelectric points.
Figure 7B:
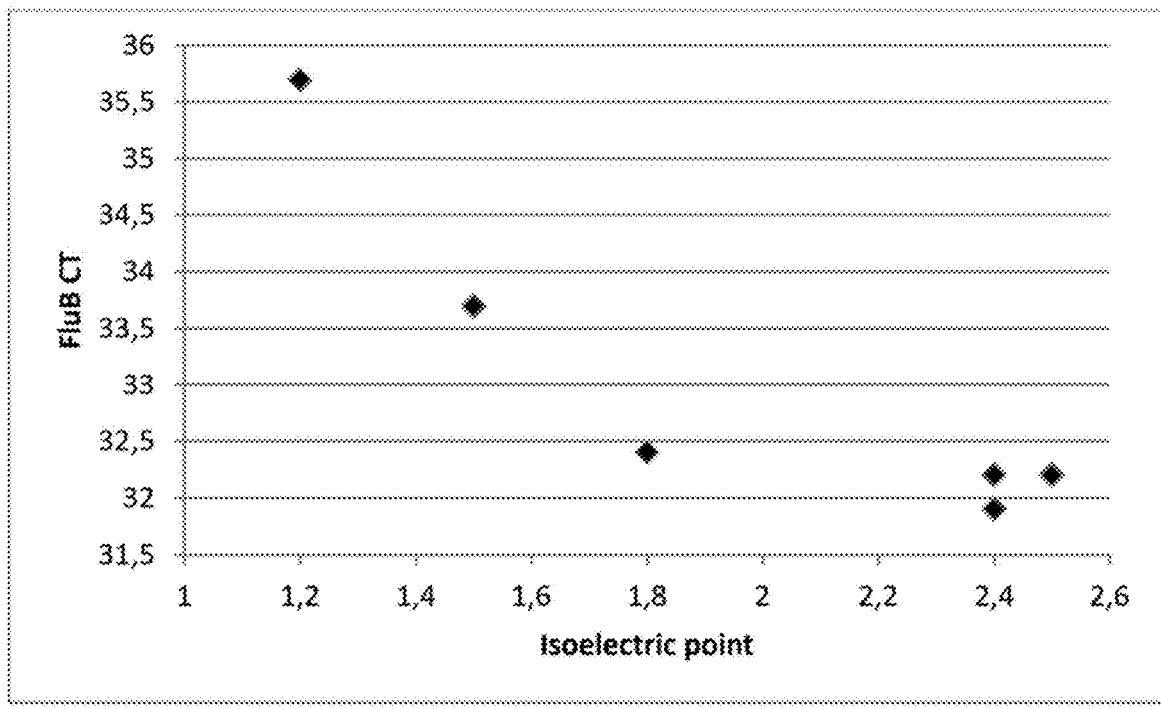
Figure 7C:
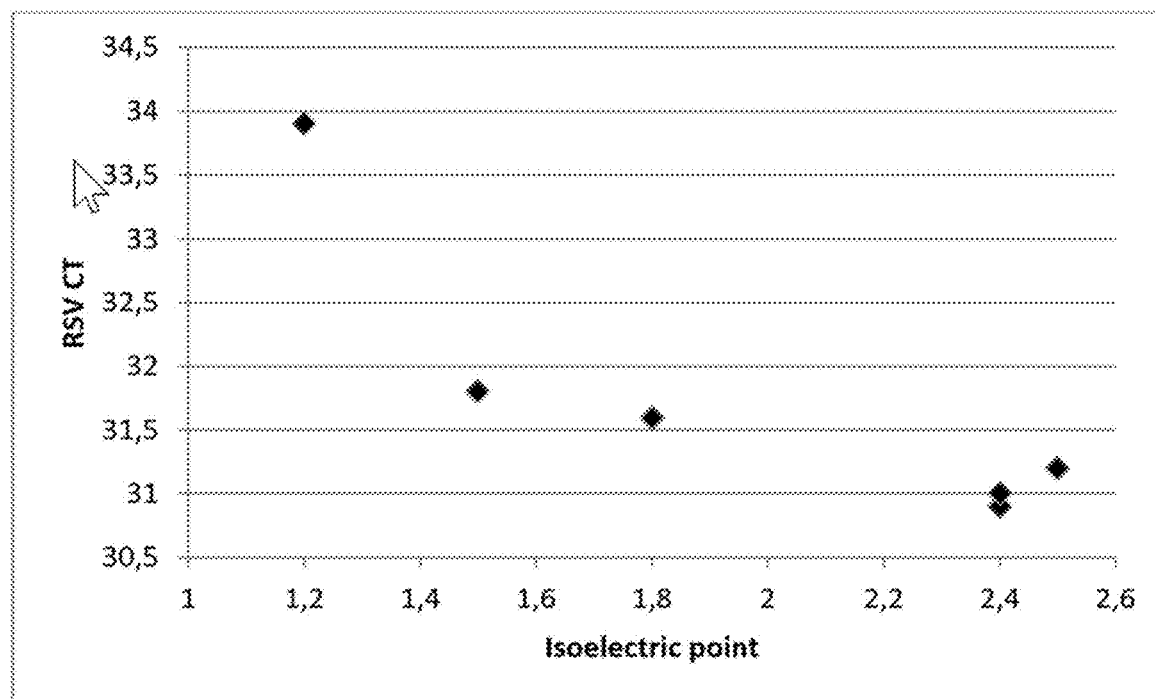
Figure 8:
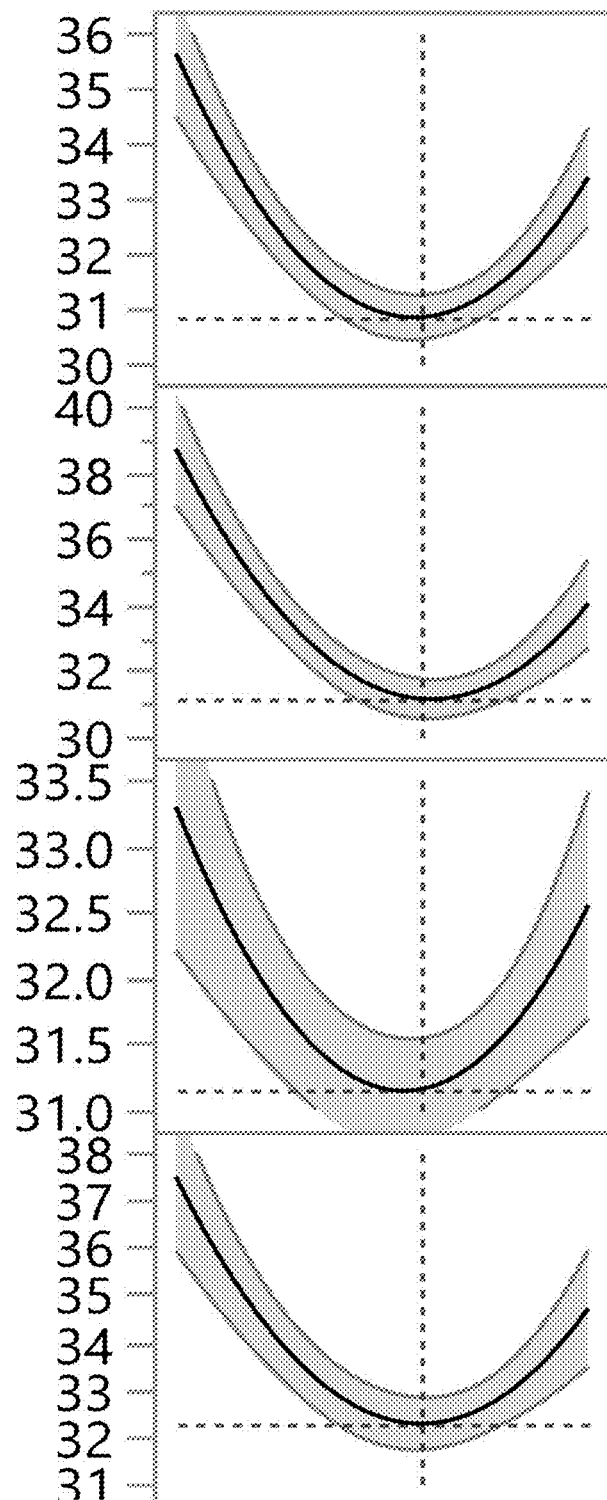
FIG. 8 illustrates the dependence of the measured FluA, FluB, RSV and Internal Positive Control (IPC) Ct values of the MC47 samples on their isoelectric points.

Subsequently, the influence of the isoelectric point of the particles on performance of the particles in COBAS® LIAT® assays were analyzed. Herein, the silica coated MC47 and MC48 beads as described above were subjected to a PCR amplification/detection reaction using the reagents from the COBAS® LIAT® FluA/B RSV test under standard conditions. The results of the measured Cycle Threshold (CT) values for MC48 beads for FluA (FIG. 7A), for FluB (FIG. 7B) and RSV (FIG. 7C) in dependence of the isoelectric point are provided in FIG. 7. In FIG. 8 the dependence of the measured FluA, FluB, RSV and Internal Positive Control (IPC) Ct values of the MC47 samples on their isoelectric points is illustrated. A summary of the Ct values generated using the MC47 and MC48 coated beads and their correlation to the isoelectric point values is provided in Table 5.

TABLE 5

FluA, FluB, RSV CT and isoelectric point values of MC47and MC48 beads.

| Sample | Isoelectric point | FluA CT | FluB CT | RSV CT |
|---|---|---|---|---|
| MC47LG1 | 2.7 | 31.1 | 31.7 | 31.0 |
| MC47LG2 | 2.6 | 30.5 | 30.5 | 31.2 |
| MC47LG3 | 2.9 | 31.0 | 30.9 | 31.4 |
| MC47LG6 | 2.5 | 30.7 | 30.8 | 31.4 |
| MC47LG7 | 2.4 | 31.4 | 32.0 | 31.0 |

TABLE 5-continued

FluA, FluB, RSV CT and isoelectric
point values of MC47and MC48 beads.

| Sample | Isoelectric point | FluA CT | FluB CT | RSV CT |
|---|---|---|---|---|
| MC47LG8 | 2.3 | 31.0 | 31.8 | 31.5 |
| MC47LG12 | 2.2 | 31.0 | 31.5 | 31.7 |
| MC47LG14 | 1.5 | 35.8 | 39.1 | 33.1 |
| MC47LG17 | 2.8 | 31.8 | 32.6 | 31.6 |
| MC47LG19 | 3.2 | 31.4 | 31.9 | 31.0 |
| MC47LG20 | 3.5 | 33.8 | 34.0 | 33.5 |
| MC47LG21 | 3.2 | 31.4 | 32.0 | 31.1 |
| MC47LG22 | 2.8 | 31.4 | 32.2 | 31.0 |
| MC48LG2 | 1.5 | 33.0 | 33.7 | 31.8 |
| MC48LG3 | 1.8 | 32.0 | 32.4 | 31.6 |
| MC48LG5 | 2.5 | 31.3 | 32.2 | 31.2 |
| MC48LG6 | 2.4 | 31.4 | 31.9 | 30.9 |
| MC48LG7 | 1.2 | 34.3 | 35.7 | 33.9 |
| MC48LG9 | 2.4 | 31.6 | 32.2 | 31.0 |

Figure 9:
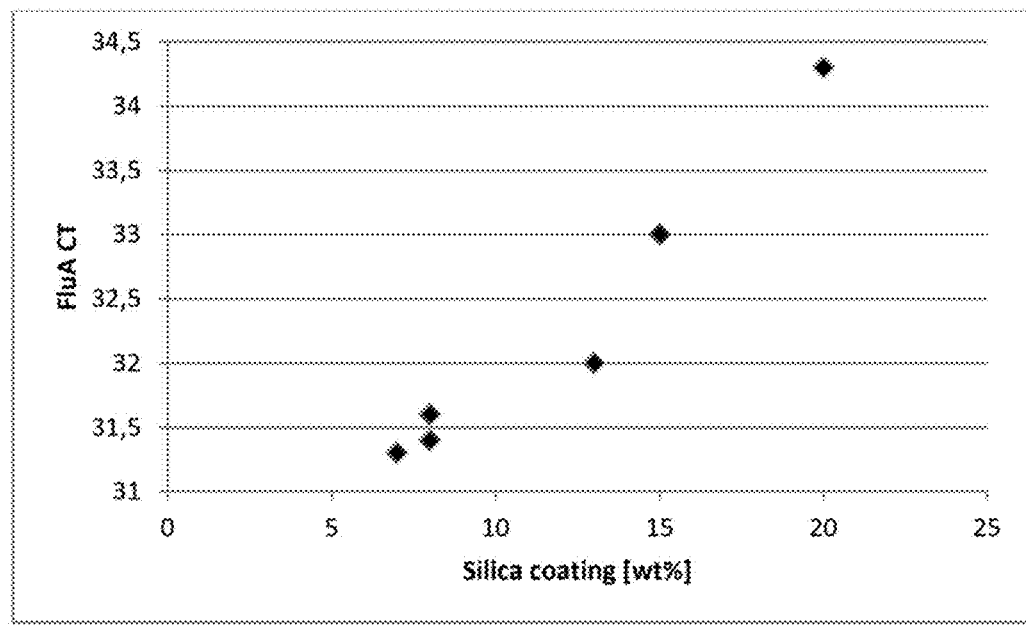
FIG. 9 illustrates the dependence of the measured FluA Ct values of the MC48 samples on the silica coating thickness.
Figure 10A:
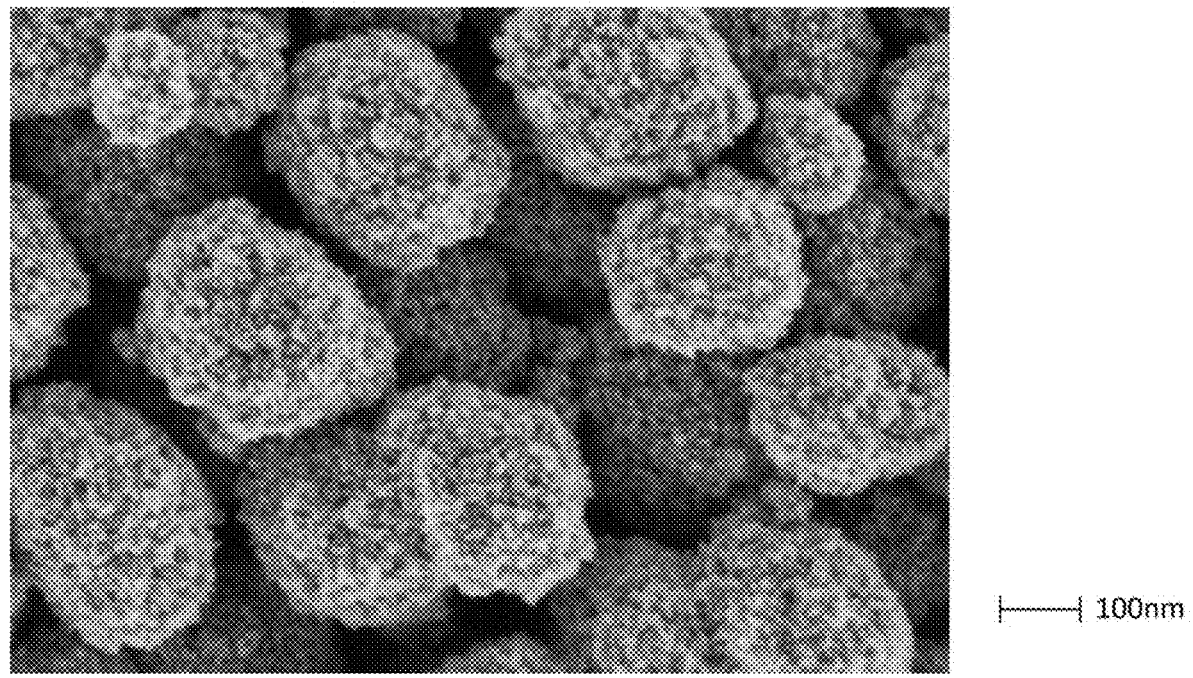
FIGS. 10A-10C illustrate the magnetic glass particles MC14 without coating (FIG. 10A), with low coating thickness of the liquid glass coating according to current disclosure (FIG. 10B), and the high coating thickness using the Tetraethyl Ortho Silicate (TEOS) coating procedure (FIG. 10C).
Figure 10B:
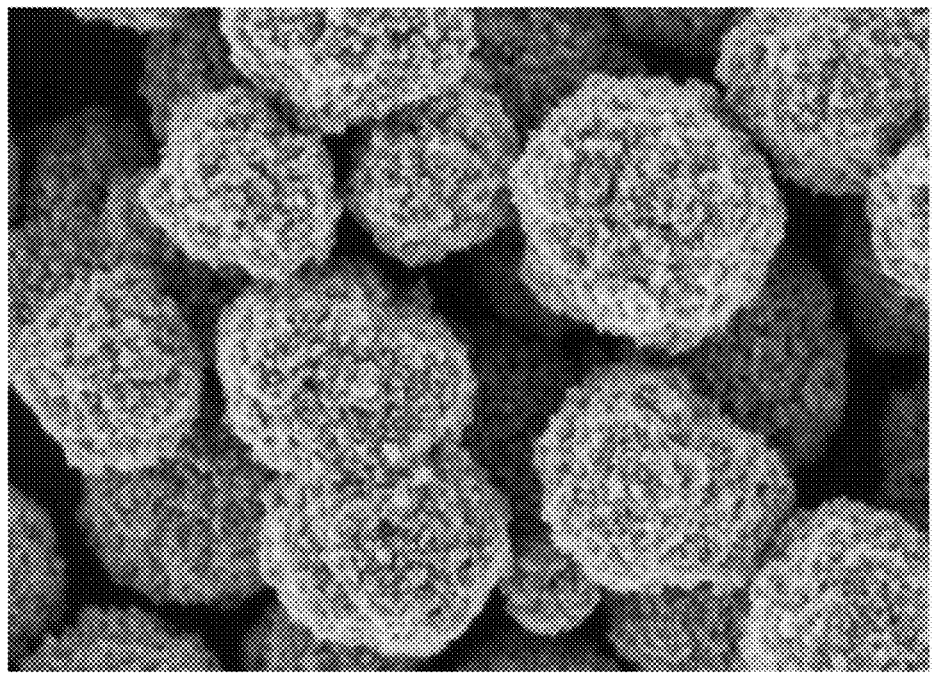
Figure 10C:
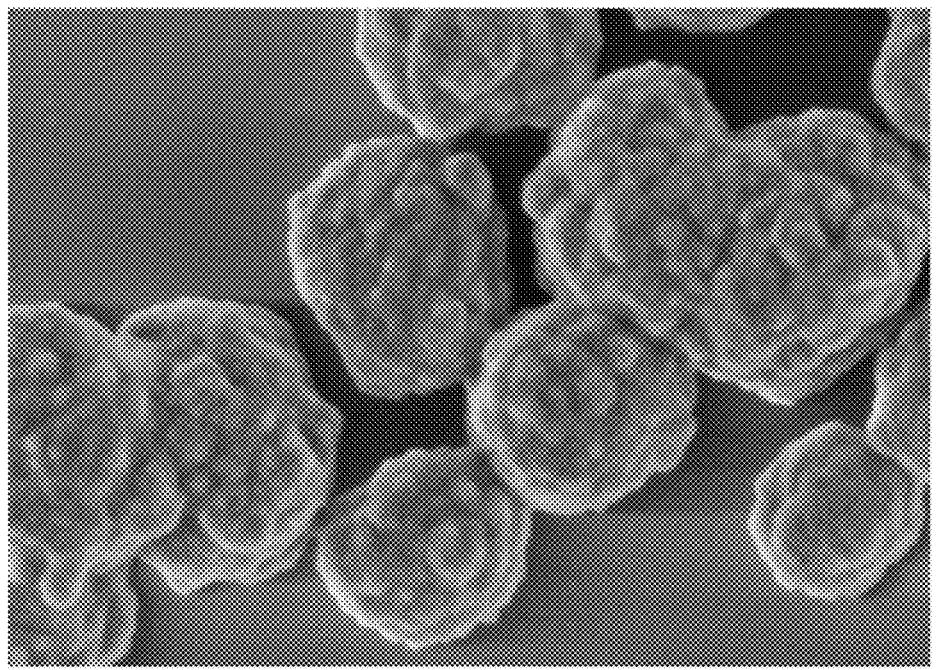

From these data it may be deduced that the performances of the particles in the COBAS® Liat® assay are depending on the isoelectric point of the particles. Moreover, it becomes apparent that both too high as well as too low isoelectric point values lead to an impaired performance of the particles. Thus, as the isoelectric point of the particles directly correlates with the coating thickness of the particles, it is very important to control the coating thickness of the particles which according to the current disclosure is done by the addition of HCl to the particle/silicate suspension. Further indication that too thick coatings lead to impaired performances of the particles in the PCR-assays is provided in FIG. 9 showing a direct correlation between coating thickness and increasing CT values. The structure of beneficial coating is directly visible looking at the SEM micrographs displayed in FIG. 10. Comparing uncoated MC14 beads (FIG. 10A), MC14 beads coated using the method according to the current disclosure (FIG. 10B) and MC14 beads coated with the TEOS method described above (FIG. 10C) it becomes apparent that the coating thickness of the liquid glass coating with sodium silicate is very thin, while the coating with TEOS provides for a substantially thicker coating. Herein, delayed Ct values of the TEOS coated beads describes above also fit the data showing that a thick coating leads to an impaired performance in PCR assays.

Summarizing, the above data clearly show that the coated beads according to the current disclosure exhibit beneficial properties over magnetic beads manufactured and coated using prior art methods. Herein, the magnetic core particles are built up by controlled aggregates of magnetite nanoparticles. With this, the particles show very low magnetic remanence combined with particle sizes in the range of 80-500 nm. The controlled aggregates are only formed by adding a stabilizer in situ in the solvothermal reaction. Moreover, the thickness of the glass coating of the particles must be specifically controlled in that too thick coatings as well as too high and too low isoelectric point values of the coated particles are to be avoided.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims.

Various publications are cited herein, the disclosures of which are incorporated by reference in their entireties.

What is claimed is:

1. A magnetic bead composition comprising (a) a stabilizer and a magnetic core produced under solvothermal conditions and (b) a liquid-glass coating;
   wherein the magnetic bead is superparamagnetic,
   wherein the magnetic core is a defined aggregate of magnetic nanoparticles, the magnetic nanoparticles having a size of 30 nm or less, and wherein the diameter of the magnetic core is between 100-400 nm, and
   wherein the liquid-glass coating comprises a silicate and has a thickness of 20 nm or less.

2. The composition of claim 1, wherein the magnetic bead has a particle size of between 200-400 nm.

3. The composition of claim 1, wherein the magnetic bead has a saturation magnetization between 50-70 $Am^2/kg$.

4. The composition of claim 1, wherein the magnetic bead has a magnetic remanence below 3 $Am^2/kg$.

5. The composition of claim 1, wherein the silicate is selected from the group consisting of sodium silicate, potassium silicate, calcium silicate, lithium silicate, and magnesium silicate.

6. The composition of claim 1, wherein the stabilizer is selected from the group consisting of citrate, histidine, cetyltrimethylammonium bromide (CTAB), cetyltrimethylammonium chloride (CTAC), sodium oleate, and polyacrylic acid.

7. The composition of claim 1, wherein the liquid-glass coating has a thickness of 10 nm or less.

8. The composition of claim 1, wherein the magnetic core is $Fe_3O_4$, $\alpha$-$Fe_2O_3$, $\gamma$-$Fe_2O_3$, $MnFe_xO_y$, $CoFe_xO_y$, $NiFe_xO_y$, $CuFe_xO_y$, $ZnFe_xO_y$, $CdFe_xO_y$, $BaFe_xO$ and $SrFe_xO$, wherein x is an integer between 1 to 3 inclusive, and wherein y is 3 or 4.

9. A suspension of magnetic beads comprising the magnetic bead composition according to claim 1 and a liquid, wherein the suspension is mixed to homogeneity.

10. The suspension of claim 9, comprising between 5-200 mg/mL magnetic beads.

11. The suspension of claim 9, wherein the liquid comprises an aqueous buffered solution.

12. The suspension of claim 11, further comprising a chaotropic agent.

13. A method of manufacturing the magnetic bead composition according to claim 1, comprising the steps of:
   (a) contacting a stabilizer and nanoparticles from any one material selected from the group consisting of metals, metal salts, metal carbides, metal nitrides, metal sulfides, metal phosphides, metal oxides, and metal chelates comprising at least one transition metal under solvothermal conditions to form the aggregate, wherein the aggregate forms a magnetic core that is superparamagnetic; and
   b) coating the magnetic core formed in step (a) with a liquid glass.

14. The suspension of claim 9, wherein the magnetic bead has a saturation magnetization between 50-70 $Am^2/kg$.

15. The suspension of claim 9, wherein the magnetic bead has a magnetic remanence below 3 $Am^2/kg$.

16. The suspension of claim 9, wherein the silicate is selected from the group consisting of sodium silicate, potassium silicate, calcium silicate, lithium silicate, and magnesium silicate.

17. The suspension of claim 9, wherein the stabilizer is selected from the group consisting of citrate, histidine, cetyltrimethylammonium bromide (CTAB), cetyltrimethylammonium chloride (CTAC), sodium oleate, and polyacrylic acid.

18. The suspension of claim 9, wherein the magnetic core is $Fe_3O_4$, $\alpha\text{-}Fe_2O_3$, $\gamma\text{-}Fe_2O_3$, $MnFe_xO_y$, $CoFe_xO_y$, $NiFe_xO_y$, $CuFe_xO_y$, $ZnFe_xO_y$, $CdFe_xO_y$, $BaFe_xO$ and $SrFe_xO$, wherein x is an integer between 1 to 3 inclusive, and wherein y is 3 or 4.

19. The suspension of claim 12, wherein the chaotropic agent is present in the suspension at a concentration of between 2-8 mol/L and wherein the chaotropic agent is selected from the group consisting of sodium iodide, sodium perchlorate, guanidinium thiocyanate, guanidinium isothiocyanate, and guanidinium hydrochlorite.

\* \* \* \* \*